US009820711B2

(12) United States Patent
Tsukuda

(10) Patent No.: US 9,820,711 B2
(45) Date of Patent: Nov. 21, 2017

(54) BREAST TOMOGRAPHY APPARATUS AND CONTROL METHOD

(71) Applicant: CANON KABUSHIKI KAISHA, Tokyo (JP)

(72) Inventor: Akira Tsukuda, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 234 days.

(21) Appl. No.: 14/630,767

(22) Filed: Feb. 25, 2015

(65) Prior Publication Data
US 2015/0257726 A1 Sep. 17, 2015

(30) Foreign Application Priority Data

Mar. 12, 2014 (JP) ................................. 2014-049313

(51) Int. Cl.
*A61B 6/03* (2006.01)
*A61B 6/04* (2006.01)
*A61B 6/00* (2006.01)

(52) U.S. Cl.
CPC .............. *A61B 6/502* (2013.01); *A61B 6/032* (2013.01); *A61B 6/035* (2013.01); *A61B 6/0414* (2013.01); *A61B 6/547* (2013.01); *A61B 6/0435* (2013.01); *A61B 6/0478* (2013.01); *A61B 6/5205* (2013.01)

(58) Field of Classification Search
CPC ....... A61B 6/032; A61B 6/035; A61B 6/0414; A61B 6/0435; A61B 6/502; A61B 6/547
USPC ...................... 378/20, 37, 288, 209, 62, 208
See application file for complete search history.

(56) References Cited

U.S. PATENT DOCUMENTS

| 5,078,142 A | * | 1/1992 | Siczek | A61B 6/0435 |
| | | | | 348/E13.014 |
| 5,289,520 A | * | 2/1994 | Pellegrino | A61B 6/0435 |
| | | | | 378/208 |
| 5,308,321 A | * | 5/1994 | Castro | A61B 6/0414 |
| | | | | 600/415 |
| 5,386,447 A | * | 1/1995 | Siczek | A61B 6/0414 |
| | | | | 378/196 |

(Continued)

FOREIGN PATENT DOCUMENTS

| JP | 2007-082908 | 4/2007 |
| JP | 2008-307236 | 12/2008 |

(Continued)

OTHER PUBLICATIONS

W. Xia et al., "An Optimized Ultrasound Detector for Photoacoustic Breast Tomography", *Med. Phys.*, vol. 40, No. 3, pp. 32901-1 through 32901-113 (Feb. 28, 2013).

*Primary Examiner* — Allen C. Ho
(74) *Attorney, Agent, or Firm* — Fitzpatrick, Cella, Harper & Scinto

(57) ABSTRACT

A breast tomography apparatus includes a gantry incorporating a radiation source and a radiation detector and a breast insert portion which is provided in the gantry and in which the breast as an imaging target is to be inserted. The breast tomography apparatus detects contact between an object and the gantry by using at least one contact detection sensor arranged on the gantry, and determines the insert condition of the breast into the breast insert portion based on the detection of contact between the object and the gantry by the contact detection sensor.

22 Claims, 20 Drawing Sheets

(56) References Cited

U.S. PATENT DOCUMENTS

| | | | |
|---|---|---|---|
| 5,415,169 A * | 5/1995 | Siczek | A61B 6/0435 348/E13.014 |
| 5,564,438 A * | 10/1996 | Merchant | A61B 6/0414 378/37 |
| 5,855,554 A * | 1/1999 | Schneider | A61B 6/0414 378/37 |
| 6,157,697 A * | 12/2000 | Mertelmeier | A61B 5/0536 378/37 |
| 6,254,614 B1 * | 7/2001 | Jesseph | A61B 6/0414 600/562 |
| 6,298,114 B1 * | 10/2001 | Yoda | A61B 6/0414 378/37 |
| 6,463,122 B1 * | 10/2002 | Moore | A61B 6/0435 378/17 |
| 6,480,565 B1 * | 11/2002 | Ning | A61B 6/032 378/20 |
| 6,748,044 B2 * | 6/2004 | Sabol | G06T 7/0012 250/363.04 |
| 6,987,831 B2 * | 1/2006 | Ning | A61B 6/032 378/20 |
| 7,298,816 B2 * | 11/2007 | Moore | A61B 6/4441 378/197 |
| 7,450,688 B2 * | 11/2008 | Becker | A61N 5/1049 378/208 |
| 7,492,858 B2 * | 2/2009 | Partain | A61B 6/032 378/196 |
| 7,519,149 B2 * | 4/2009 | Mackie | A61N 5/1042 378/37 |
| 7,526,066 B2 * | 4/2009 | Koshnitsky | A61B 6/0414 378/203 |
| 7,561,661 B2 * | 7/2009 | Ullberg | A61B 6/032 378/19 |
| 7,597,104 B2 * | 10/2009 | Zheng | A61B 6/04 128/869 |
| 7,649,981 B2 * | 1/2010 | Seppi | A61B 6/032 378/124 |
| 7,656,993 B2 * | 2/2010 | Hoernig | A61B 6/0414 128/845 |
| 7,668,287 B2 * | 2/2010 | Sendai | A61B 5/0091 378/15 |
| 7,742,796 B2 * | 6/2010 | Eberhard | A61B 6/502 378/37 |
| 7,763,864 B2 * | 7/2010 | Formenti | A61B 6/0414 128/845 |
| 7,764,762 B2 * | 7/2010 | Sendai | A61B 5/0091 378/19 |
| 7,831,015 B2 * | 11/2010 | Li | A61B 6/032 378/37 |
| 7,864,918 B2 * | 1/2011 | Schilling | A61B 5/704 378/196 |
| 7,869,862 B2 * | 1/2011 | Seppi | A61B 6/032 600/420 |
| 7,945,020 B2 * | 5/2011 | Jan | A61B 6/502 378/209 |
| 7,957,503 B2 * | 6/2011 | Kobayashi | A61B 6/0414 378/209 |
| 7,957,508 B2 * | 6/2011 | Brooks | A61B 6/502 378/37 |
| 7,978,812 B2 * | 7/2011 | Thaler | A61B 6/0414 378/208 |
| 8,130,906 B2 * | 3/2012 | Sendai | A61B 6/0435 378/37 |
| 8,139,712 B2 * | 3/2012 | Kojima | A61B 6/0414 378/116 |
| 8,194,819 B2 * | 6/2012 | Eliasson | A61B 6/025 378/189 |
| 8,374,312 B2 * | 2/2013 | Mansfield | A61B 6/0414 378/20 |
| 8,454,530 B2 * | 6/2013 | Nakata | A61B 6/502 600/564 |
| 8,649,479 B2 * | 2/2014 | De Man | A61B 6/032 378/16 |
| 8,712,012 B2 * | 4/2014 | O'Connor | A61B 6/03 378/208 |
| 8,804,903 B2 * | 8/2014 | Hoernig | A61B 6/0435 378/208 |
| 8,824,625 B2 * | 9/2014 | Ullberg | A61B 6/0435 378/19 |
| 8,842,806 B2 * | 9/2014 | Packard | A61B 6/025 378/195 |
| 8,855,745 B2 * | 10/2014 | Hoernig | A61B 6/032 600/431 |
| 9,161,733 B2 * | 10/2015 | Koehler | A61B 6/484 |
| 9,380,990 B2 * | 7/2016 | Kim | A61B 6/502 |
| 9,414,801 B2 * | 8/2016 | Kim | B25J 9/1694 |
| 2007/0071299 A1 | 3/2007 | Matsuura | 328/128 |

FOREIGN PATENT DOCUMENTS

| | | |
|---|---|---|
| JP | 2012-130542 | 7/2012 |
| JP | 2013-022041 | 2/2013 |

* cited by examiner

● ■ : CONTACT
◐ ▨ : NON-CONTACT

● ■ : CONTACT

⊘ ▨ : NON-CONTACT

● ■ : CONTACT

⊘ ▨ : NON-CONTACT

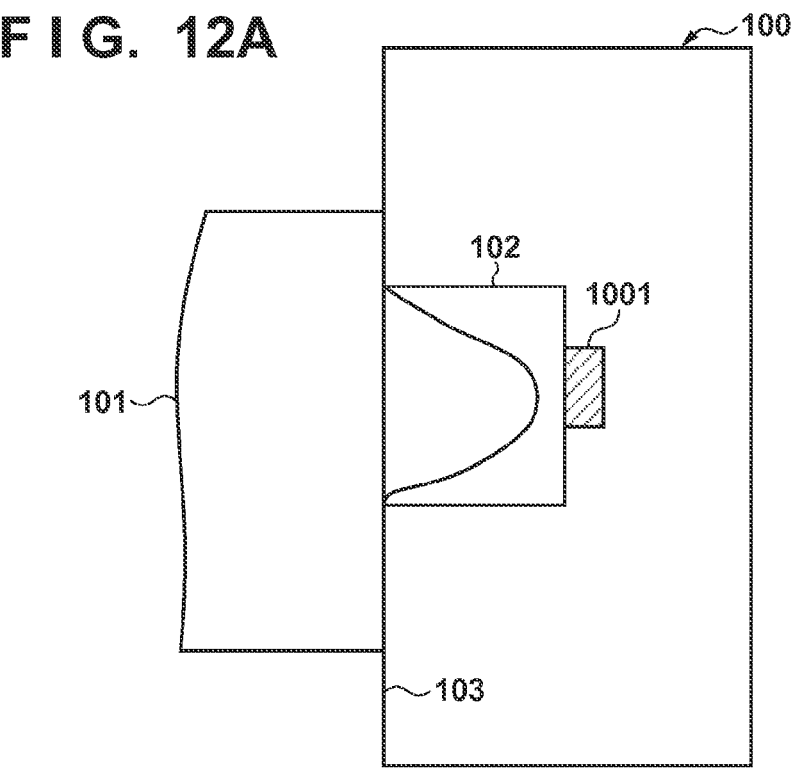
F I G. 12A
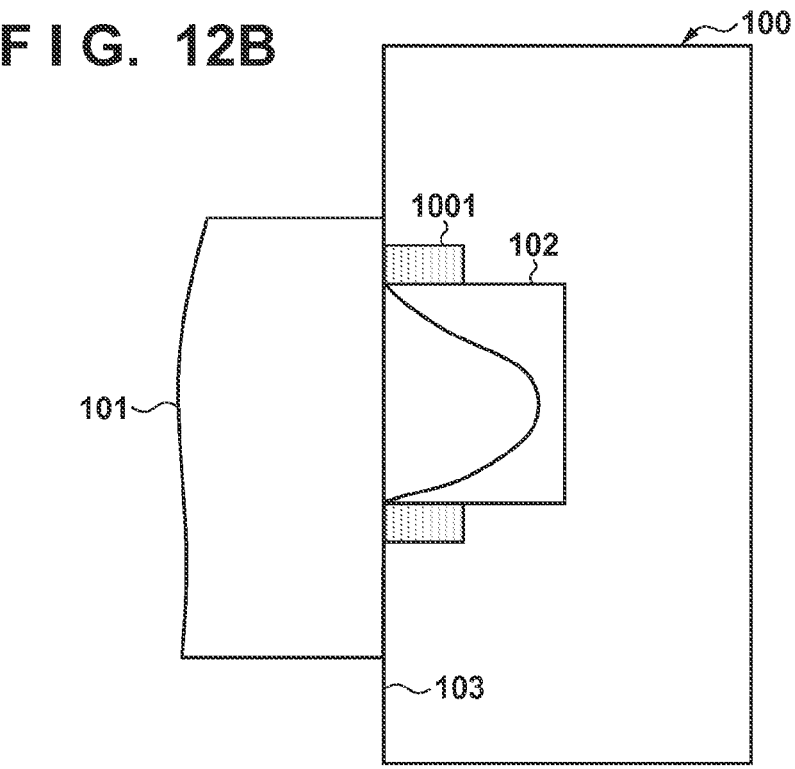
F I G. 12B

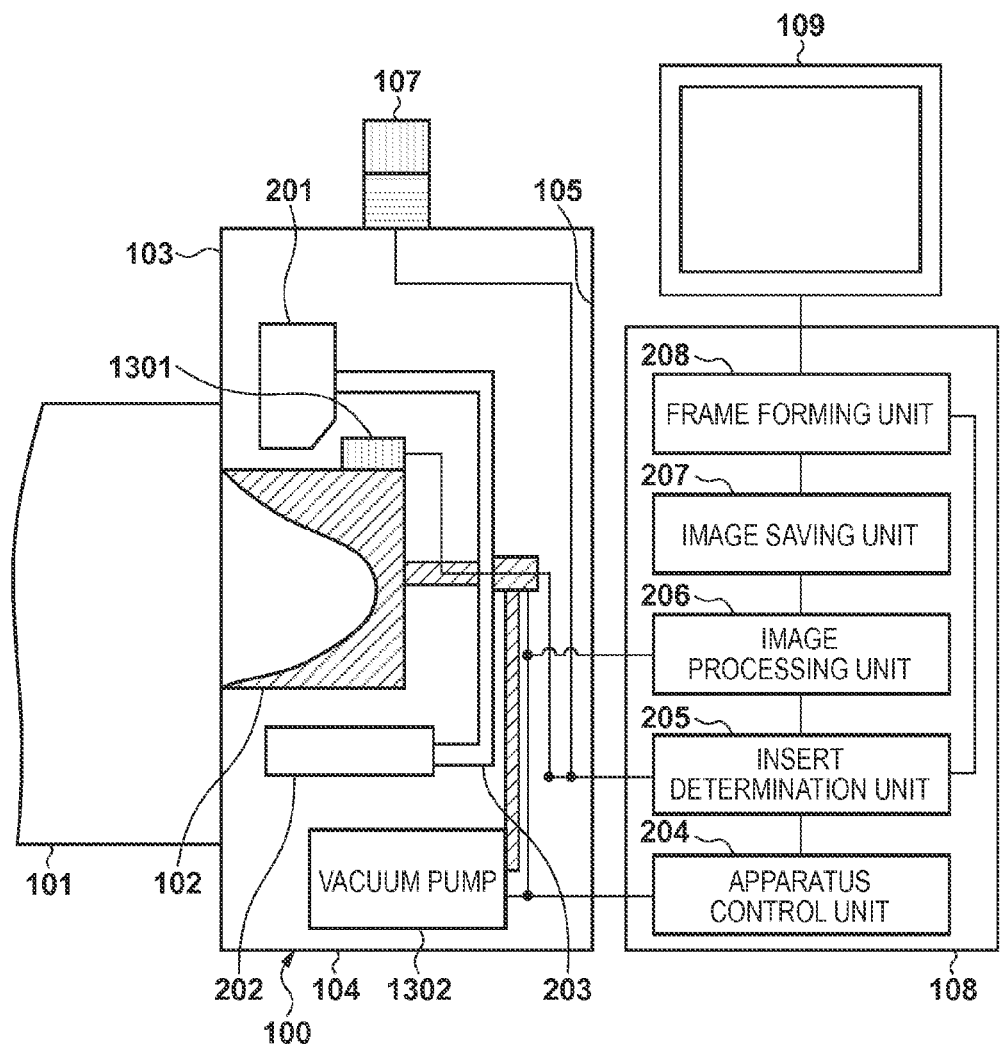

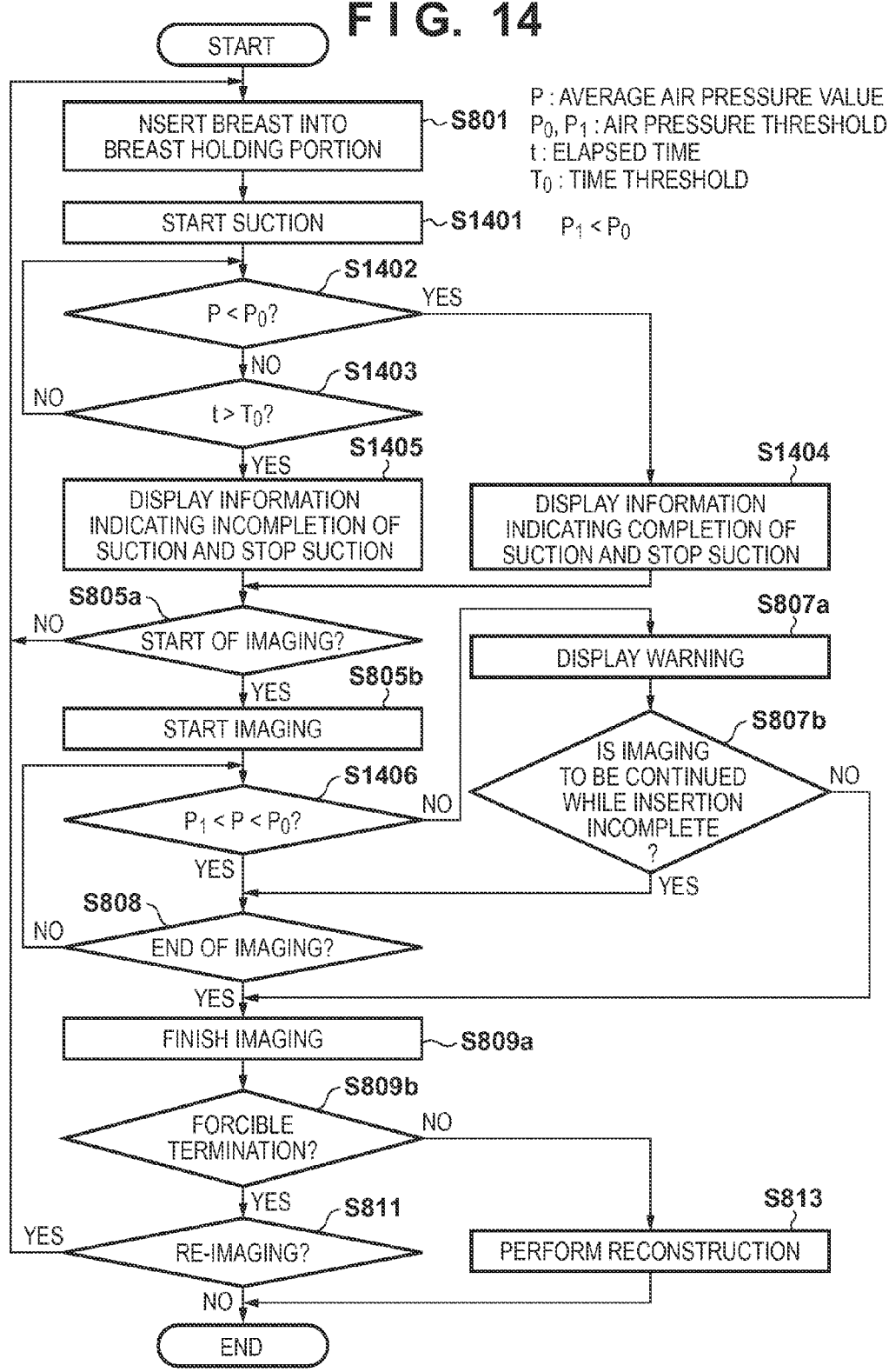

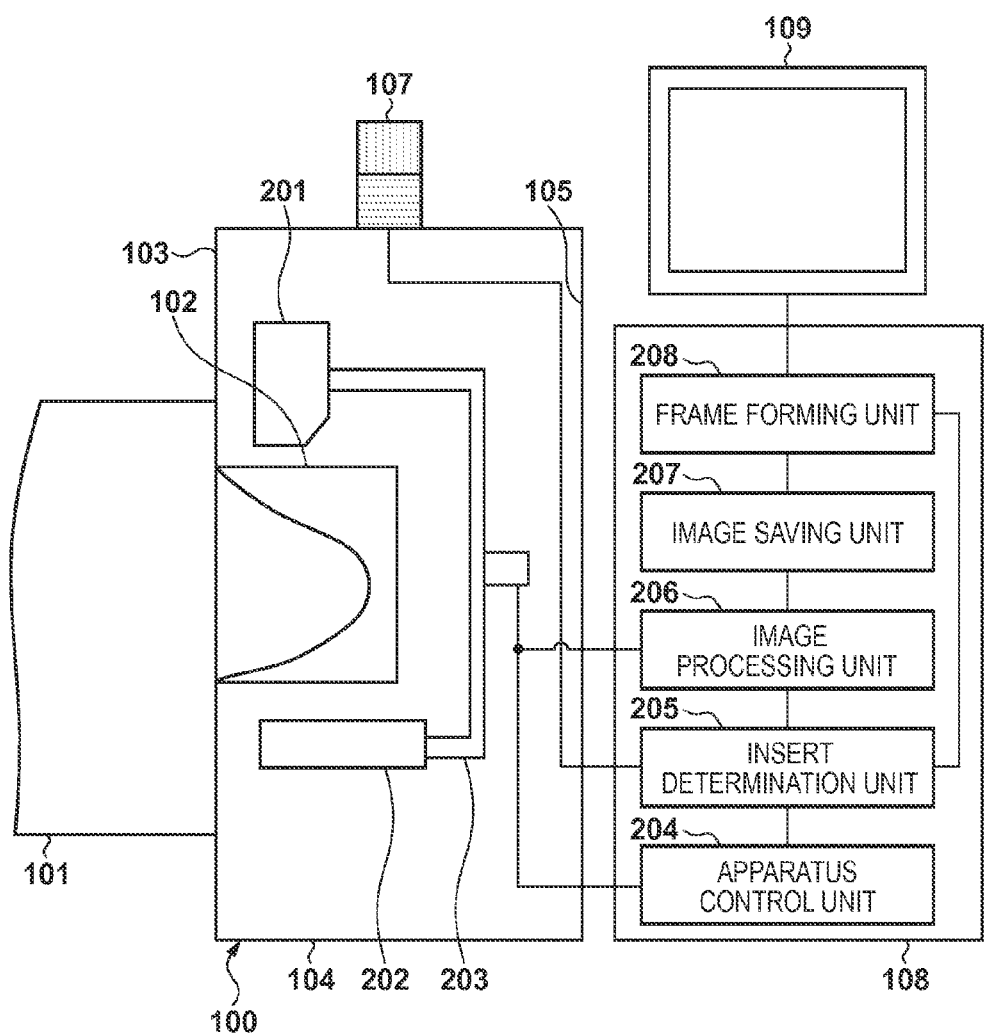

F I G. 16A
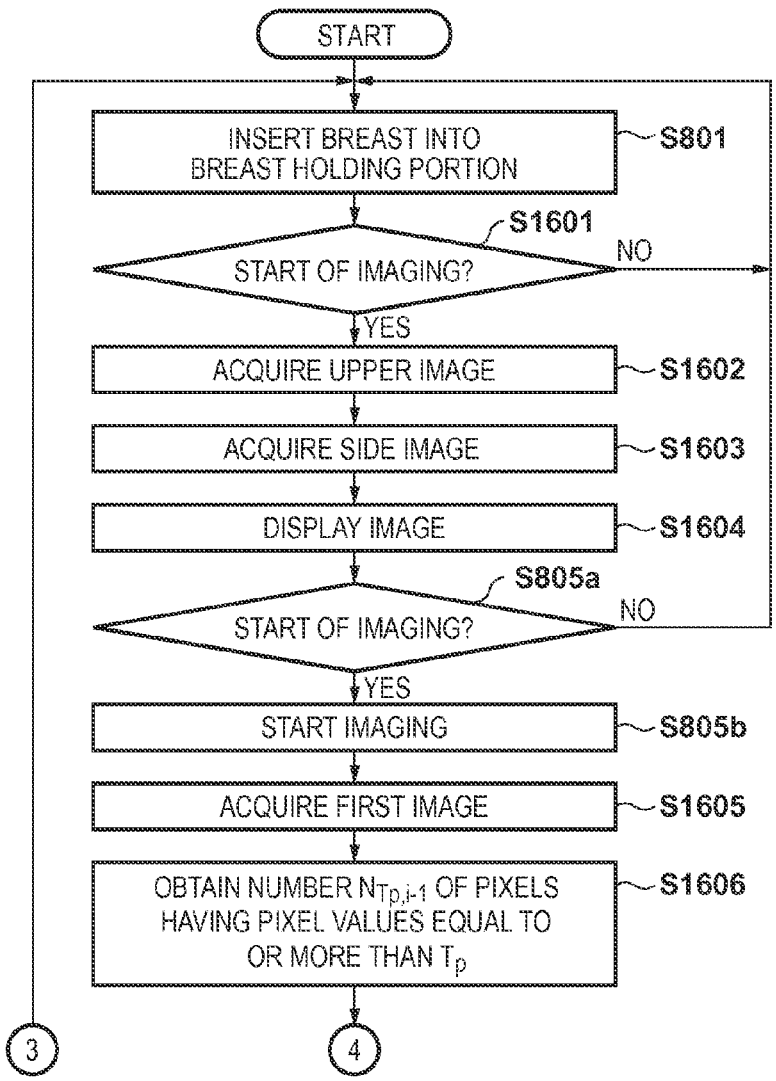

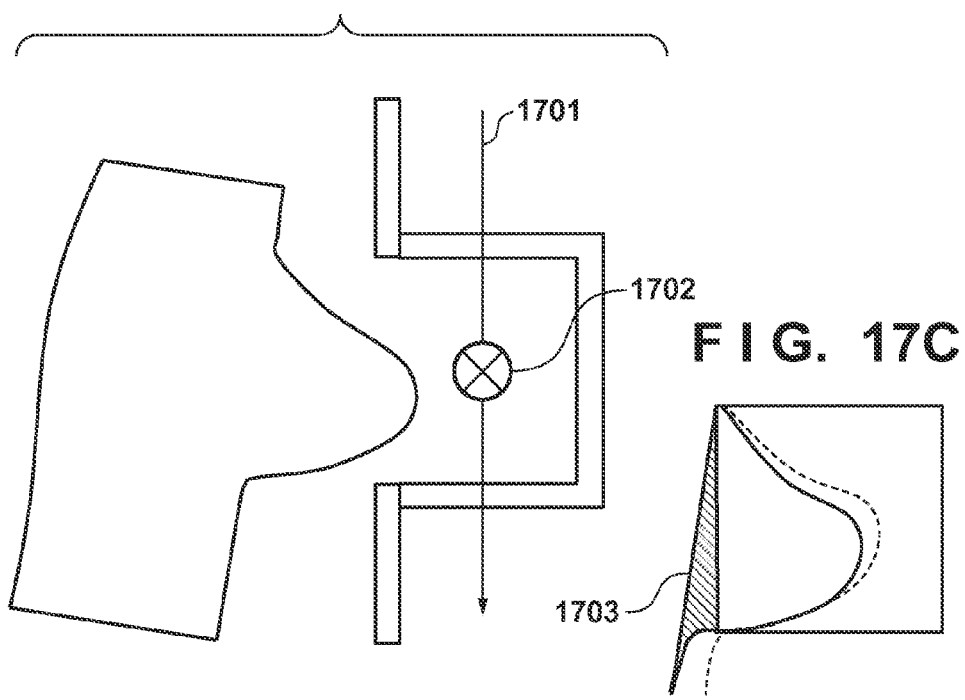
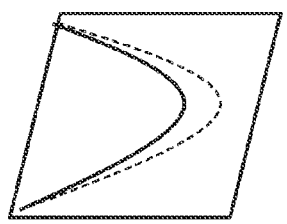
BROKEN LINE : POSITION OF BREAST
              IN PROPER POSTURE
SOLID LINE :  POSITION OF BREAST
              IN POSTURE LEANING FORWARD

BREAST TOMOGRAPHY APPARATUS AND CONTROL METHOD

BACKGROUND OF THE INVENTION

Field of the Invention

The present invention relates to a breast tomography apparatus and a control method.

Description of the Related Art

As an apparatus for finding breast cancer, a breast-specific tomography apparatus (to be referred to as a breast tomography apparatus hereinafter) is available. In this breast tomography apparatus, the breast is inserted into the breast insert portion provided in a gantry, and a radiation generator and a radiation detector are rotated to acquire a plurality of projection images of the breast. A tomographic image is then acquired by reconstructing the projection images. In order to acquire tomographic images sufficient for diagnosis, such a breast tomography apparatus needs to acquire images of the overall breast including a portion near the chest wall of the human body. For this purpose, it is necessary to check, before the start of projection imaging, that the overall breast including a portion near the chest wall is sufficiently deeply inserted into the breast insert portion. If the breast is not sufficiently deeply inserted, it is necessary to perform re-imaging upon checking the insertion of the breast again so as to image a portion near the chest wall.

Japanese Patent Laid-Open No. 2013-22041 (to be referred to as patent literature 1 hereinafter) discloses a method of checking such an insert condition of the breast. In addition, methods of detecting body motions are disclosed in patent literature 1 and Japanese Patent Laid-Open No. 2007-82908 (to be referred to as patent literature 2 hereinafter). Patent literature 1 discloses a technique of specifying the position of a breast of an object by detecting the depth from the insert opening. This literature also describes a technique of detecting a change in the depth of the breast and monitoring the body motion of the object by always monitoring the depth. Patent literature 2 discloses a method of determining the presence/absence of a body motion by performing subtraction with respect to a given acquired image and an image acquired before the acquired image for each pixel and comparing the sum of the absolute values of the differences with a threshold.

There are individual difference in breast size among objects. For this reason, even breasts inserted sufficiently deeply differ in the depth from the insert opening. If, for example, the size of the breast is larger than the average size, the depth from the insert opening, which the breast reaches, is larger than the average depth. This makes it sometimes inaccurate to determine that the overall breast is sufficiently deeply inserted into the imaging target insert portion by using the method disclosed in patent literature 1.

According to patent literature 2, it is necessary to save an image for subtraction other than an obtained image in a storage device, among storage devices, which enables fast access, such as a DRAM (Dynamic Random Access Memory). Such a storage device enabling fast access has its own limit on storage capacity. If, therefore, this storage device holds images used for subtraction for the above body motion detection, the storage capacity used for other purposes decreases. In addition, a large amount of images are acquired in tomography, and hence performing subtraction with respect to all the pixels leads to a decrease in image processing speed.

SUMMARY OF THE INVENTION

According to one aspect of the present invention, there is provided a breast tomography apparatus comprising: a gantry incorporating a radiation source and a radiation detector; a breast insert portion which is provided in the gantry and in which a breast as an imaging target is to be inserted; a detection unit which is arranged on the gantry and includes a contact detection sensor configured to detect contact with an object; and a determination unit configured to determine an insert condition of the breast into the breast insert portion based on detection of contact by the contact detection sensor.

Further features of the present invention will become apparent from the following description of exemplary embodiments with reference to the attached drawings.

BRIEF DESCRIPTION OF THE DRAWINGS

FIGS. 12A and 12B are views each showing an example of the arrangement of an illuminance detection unit according to the third embodiment;

FIG. 13 is a view showing an example of the schematic arrangement of a breast tomography apparatus according to the fourth embodiment;

FIG. 14 is a flowchart showing an example of a procedure in the breast tomography apparatus according to the fourth embodiment;

FIG. 15 is a view showing an example of the schematic arrangement of a breast tomography apparatus according to the fifth embodiment;

FIGS. 16A and 16B are flowcharts showing an example of a procedure in the breast tomography apparatus according to the fifth embodiment;

FIGS. 17A to 17C are views for explaining the relationship between an obtained image and the posture of an object according to the fifth embodiment.

DESCRIPTION OF THE EMBODIMENTS

Several embodiments of the present invention will be described in detail below with reference to the accompanying drawings.

<First Embodiment>

Figure 1A:
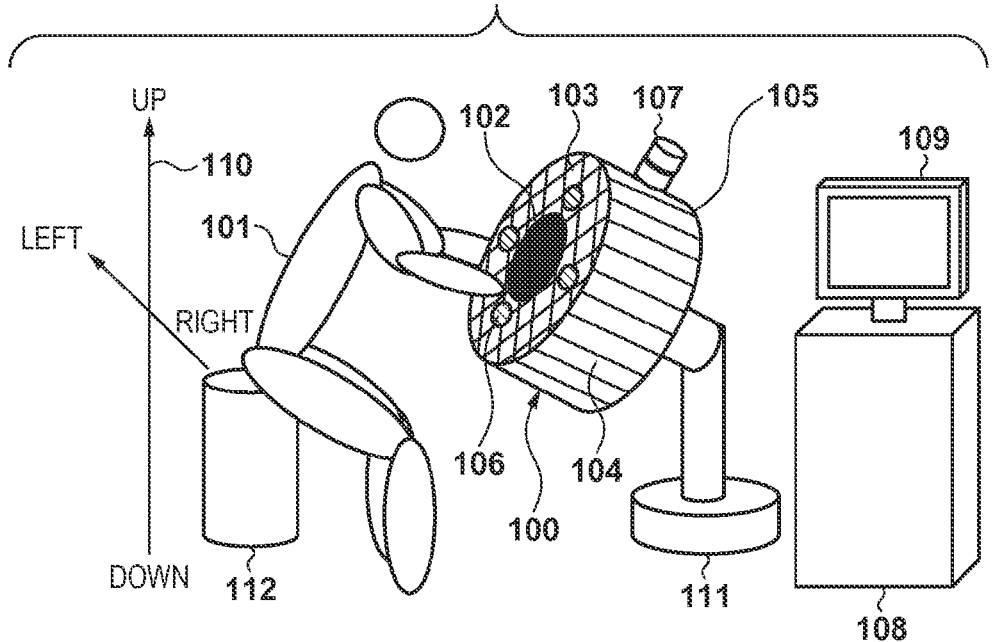
FIGS. 1A and 1B are perspective views each showing an example of the outer appearance of a breast tomography apparatus according to the first embodiment.
Figure 1B:
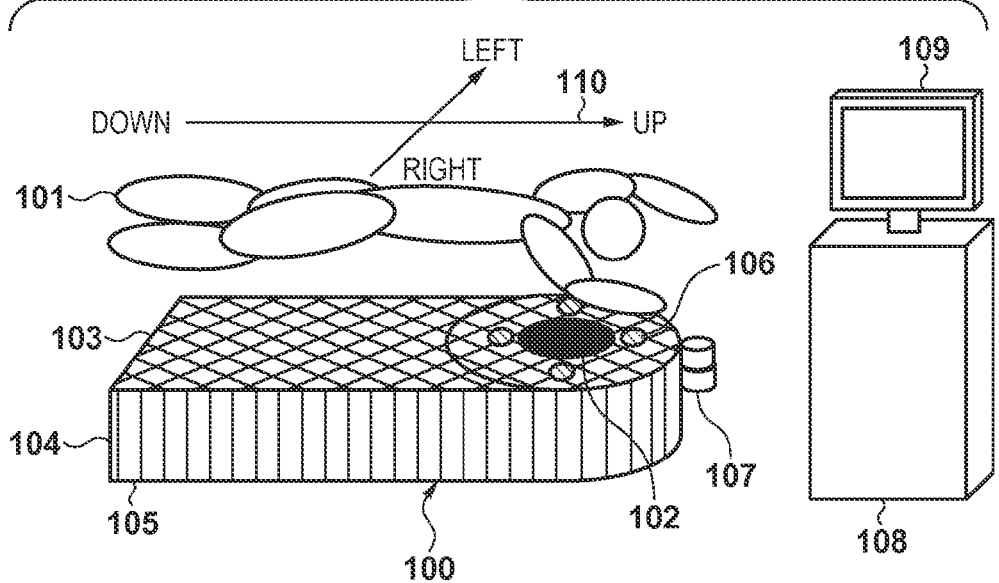

FIGS. 1A and 1B are views each showing an example of the outer appearance of a breast tomography apparatus according to the first embodiment. Referring to FIG. 1A, an object 101 in a sitting posture is imaged. Referring to FIG. 1B, the object in a prone posture is imaged. A breast tomography apparatus designed to perform imaging in a sitting posture like that shown in FIG. 1A is called a sitting posture type apparatus. A breast tomography apparatus designed to perform imaging in a prone posture like that shown in FIG. 1B is called a prone posture type apparatus.

A gantry 100 incorporates a radiation source and a radiation detector, and includes a breast insert portion 102 for the insertion of the breast of the object 101 as an imaging target. The breast insert portion 102 has a function of holding the breast, and hence can also be termed a breast holding portion. The breast insert portion 102 is, for example, a cylindrical hole provided in the front surface of the gantry 100 (gantry front part 103). The breast of an object 101 as an imaging target is inserted and held in the breast insert portion 102 during imaging. Note that a method of fixing the breast in the breast insert portion 102 is sometimes used during imaging. For example, Japanese Patent Laid-Open No. 2008-307236 (to be referred to as literature 3 hereinafter) discloses a method of fixing the breast in the breast insert portion 102 by decompressing the breast insert portion 102 using a suction mechanism. Such an arrangement may be applied to this embodiment.

The surface of the gantry 100 of the breast tomography apparatus, which faces an object 101, will be referred to as the gantry front part 103. The side surface portion of the gantry 100 will be referred to as a gantry side part 104. The rear surface portion of the gantry 100 will be referred to as a gantry rear part 105. In the prone posture type apparatus, the gantry front part 103, the gantry side part 104, and the gantry rear part 105 include portions required to support the object 101, as shown in FIG. 1B. In the prone posture type apparatus, part of the gantry 100 (for example, the gantry front part 103) is sometimes formed as a base such as a bed.

At the time of imaging, in both the sitting posture type apparatus in FIG. 1A and the prone posture type apparatus in FIG. 1B, the gantry front part 103 contacts, for example, peripheral portions of the breast as an imaging target, the abdomen of the object 101, a shoulder of the object 101, and the breast which is not an imaging target. The gantry 100 (the gantry front part 103 in this embodiment) is provided with at least one contact detection sensor (to be referred to as a contact detection unit 106 hereinafter) for detecting contact with the object 101. Contact detection units 106 are arranged, for example, at positions to detect contact with peripheral portions of the breast as an imaging target or the chest of the object 101, the abdomen of the object 101, and a shoulder of the object 101. The placement of the contact detection units 106 will be described later. In this embodiment, the insert condition of the breast into the breast insert portion 102 is determined based on the detection of contact by the contact detection sensors.

The gantry side part 104 is provided with an insert display unit 107 for displaying the insert condition of the breast as an imaging target into the breast insert portion 102. Note that the position of the insert display unit 107 is not limited to the gantry side part 104. For example, the insert display unit 107 may be provided on the gantry front part 103 or the gantry rear part 105. The insert display unit 107 is formed from, for example, a warning light such as a lamp, and indicates proper contact between the contact detection unit 106 and an object. Alternatively, a liquid crystal display or the like may be used as the insert display unit 107. When using a liquid crystal display, it is possible to present an operator such as a radiological technician with more detailed information about a contact state with the object 101, for example, displaying a specific portion which is not in contact.

An operator such as a radiological technician can check information indicating, for example, whether the breast of an object is sufficiently deeply inserted, on the insert display unit 107 provided on the gantry 100, while performing postural adjustment of the object. Checking an insert condition on the insert display unit 107 makes it unnecessary for the operator to check on a display device 109 installed in a room different from a room in which radiation is applied (the breast tomography apparatus is installed). This can facilitate checking the insert condition of the breast. Note that the same effect can be obtained by installing the insert display unit 107 inside the room in which radiation is applied. In addition, installing the insert display unit 107 outside the room in which radiation is applied allows the operator to grasp the insert condition of the breast into the breast insert portion 102 during imaging while staying outside the room in which radiation is applied. Therefore, the operator can quickly grasp the occurrence of a problem in the insert condition even during imaging, and hence can stop radiation irradiation more quickly.

The breast tomography apparatus further includes a computer 108 for image processing, control on the apparatus, and the like and the display device 109 for displaying processed images and the state of the apparatus. The computer 108 includes a CPU, a ROM, and a RAM (none of which are shown), and executes each processing (to be described later) by causing the CPU to execute programs stored in the ROM and the RAM. As the display device 109, for example, a general display such as a liquid crystal display is used. In addition, the display device 109 can also function as an input device for issuing instructions to the computer 108. When also functioning as an input device, the display device 109 is constituted by a touch panel and the like. When not functioning as an input device, the display device 109 is separately provided with devices for inputting user's instructions to the computer 108, for example, a mouse and a keyboard. Note that the display device 109 can also function as the insert display unit 107. That is, the display device 109 may also display the insert condition of the breast like the insert display unit 107. A device which informs the insert condition of the breast, such as the insert display unit 107 or the display device 109, will be referred to as an insert informing unit.

The sitting posture type breast tomography apparatus shown in FIG. 1A is provided with a gantry holding arm 111 for supporting the gantry 100 and a stool 112 for making an object take a sitting posture. Although the sitting posture type breast tomography apparatus and the prone posture type breast tomography apparatus are shown in the accompanying drawings, it is obvious that the present invention can be applied to apparatuses designed to make objects take postures other than sitting and prone postures, such as breast tomography apparatuses designed to perform imaging in a standing posture, a supine posture, and the like. Note that in this specification, "up", "down", "left", and "right" are set as denoted by reference numeral 110 in FIGS. 1A and 1B. That is, in this embodiment, "up" indicates the head side of an object, "down" indicates the foot side of the object, "right" is defined as right when seen from the object, and "left" is defined as left when seen from the object.

The functional arrangement of the first embodiment will be described next with reference to FIG. 2. The interior of the gantry 100 (to be referred to as the gantry interior hereinafter) surrounded by the breast insert portion 102, the gantry front part 103, the gantry side part 104, and the gantry rear part 105 includes devices for performing radiography. More specifically, a radiation source 201 (radiation tube), a radiation detector 202, and an arm 203 which holds the radiation source 201 and the radiation detector 202 are arranged in the gantry interior. These devices are connected to the computer 108. Note that the gantry interior may be provided with other devices, for example, a pump for implementing the above suction mechanism. In addition, the gantry 100 can incorporate the computer 108.

The radiation source 201 and the radiation detector 202 are fixed to the arm 203. The arm 203 is rotatable, and can rotate through an angle necessary for the generation of a tomographic image (for example, 360°+cone angle). The gantry 100 incorporates mechanisms (not shown) such as a motor necessary for the rotation of the arm 203.

The computer 108 implements an apparatus control unit 204, an insert determination unit 205, an image processing unit 206, an image saving unit 207, and a frame forming unit 208. The computer 108 includes a processor (CPU) and storage devices (ROM and RAM) which are required to implement these components, and implements the functions of the respective units by causing the processor to execute the programs stored in the storage devices. Note that the functions of the respective components each may be implemented by discrete hardware including a dedicated processor and a storage device.

The apparatus control unit 204 controls the rotation of the arm 203. The apparatus control unit 204 is electrically connected to a motor or the like necessary for the rotation of the arm 203, and acquires the current rotational angle from the rotation state of the motor, such as an angle, angular velocity, and angular acceleration. In addition, the apparatus control unit 204 issues instructions concerning, for example, the operation start and end of the radiation source 201 and the radiation detector 202.

The insert determination unit 205 is connected to the contact detection unit 106, the insert display unit 107, the apparatus control unit 204, the image processing unit 206, and the frame forming unit 208. The insert determination unit 205 determines the insert condition of the breast into the breast insert portion 102 based on the detection of contact by the contact detection unit 106. The insert determination unit 205 also determines the presence/absence or degree of contact detected by the contact detection unit 106, and issues instructions concerning operations to the insert display unit 107, the apparatus control unit 204, the image processing unit 206, and the frame forming unit 208. In this embodiment, when the insert determination unit 205 is implemented by using the computer in the above manner, constituent elements of the computer such as a processor and a storage device are used to implement the insert determination unit 205. Note that operation instructions corresponding to detected contact will be described later.

The image processing unit 206 performs preprocessing necessary for reconstruction, such as offset correction, gain correction, defect correction, and logarithmic conversion, with respect to an acquired image, and then performs reconstruction, thereby obtaining a tomographic image. Note that the algorithm to be used for reconstruction is not specifically limited. For example, it is possible to use a general method such as analytical reconstruction including a filtered back-projection method or algebraic reconstruction using an inverse matrix or sequential method. The image processing unit 206 performs determination concerning the execution of reconstruction based on the degree of contact sent from the insert determination unit 205. Determination concerning the execution of reconstruction will be described later.

The image saving unit 207 saves an image (tomographic image) after reconstruction which is generated by the image processing unit 206. Obviously, the image saving unit 207 may save images before reconstruction, images before correction, and the like as needed. In addition, offset images, gain images, and images indicating the positions of defects, which are required for various types of corrections, are saved in the image saving unit 207, and are read out, as needed, when the image processing unit 206 performs correction.

When saving an image, the image saving unit 207 associates the degree of insertion determined by the insert determination unit 205 with the image to be saved (an image after reconstruction, an image before reconstruction, an image before correction, or the like). For example, the degree of insertion and an image are associated by a method of embedding 0 in a header portion of the image if the breast is properly inserted to the end; otherwise, embedding 1 in the header portion. Alternatively, it is possible to prepare a file different from that of the image and save information concerning the association and information concerning the degree of insertion in the prepared file. In addition, although information concerning the degree of insertion is saved in the image saving unit 207 in this embodiment, the present invention is not limited to this. Obviously, this information may be saved in a storage device other than the image saving unit 207.

The frame forming unit 208 generates an image for the display of an image saved in the image saving unit 207 on the display device 109. The frame forming unit 208 is formed from an image processing device such as a graphic board. In addition, the frame forming unit 208 can perform display concerning the contact state received from the insert determination unit 205 and display for informing the insert condition of the breast.

The necessity to provide the contact detection units 106 on the gantry front part 103 in the first embodiment will be described next. The condition in which the breast is sufficiently deeply inserted indicates a condition in which the breast cannot be inserted deep beyond a certain condition. Note that when the gantry front part 103, especially, a portion near the breast insert portion 102, is in contact with peripheral portions of the breast as an imaging target, the breast cannot be inserted deep beyond this condition. FIG. 3 shows this state.

Figure 3A:
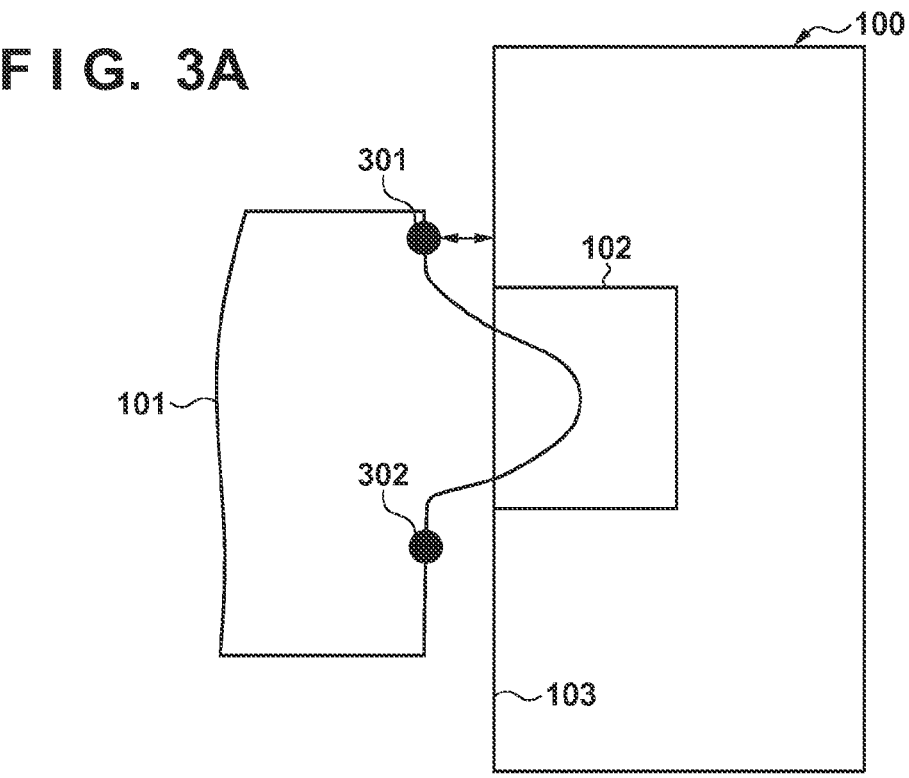
FIGS. 3A and 3B are views each for explaining a state in which the breast is sufficiently deeply inserted.
Figure 3B:
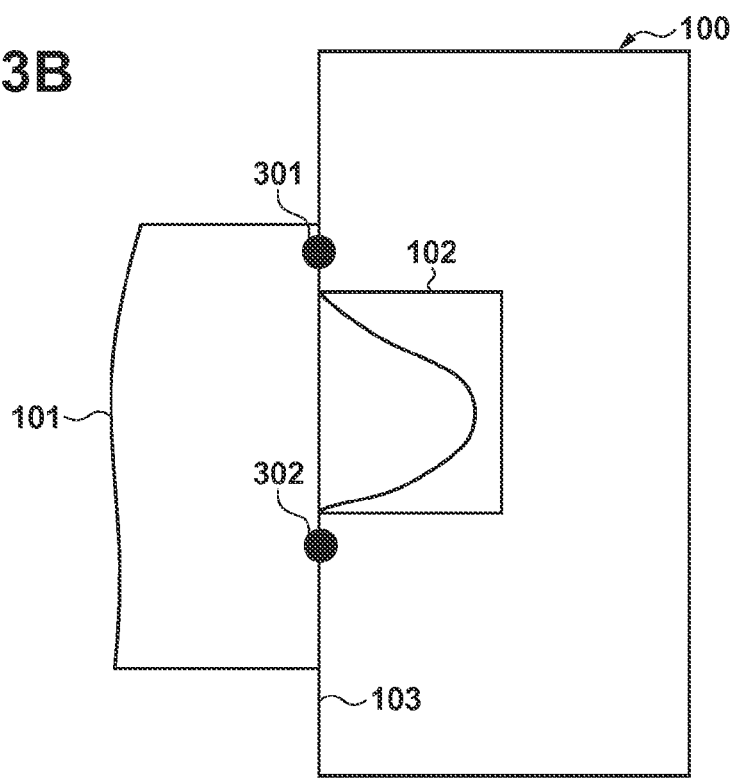

Referring to FIG. 3A, the gantry front part 103 is not in contact with the object 101 (peripheral portions 301 and 302 of the breast as an imaging target). In this case, the object 101 can insert the breast more deeply. Referring to FIG. 3B, the peripheral portions 301 and 302 of the breast as an imaging target are in contact with the gantry front part 103. In this case, the object cannot insert the breast more deeply by being blocked by the peripheral portions 301 and 302 of the breast as an imaging target.

As described above, when the gantry front part 103, especially, a portion near the breast insert portion 102 of the gantry front part 103, is in contact with the peripheral portions 301 and 302 of the breast as an imaging target, the breast has been sufficiently deeply inserted. It is therefore possible to check whether the breast is inserted to a sufficient depth, by providing the contact detection units 106 at portions where the peripheral portions 301 and 302 of the breast as an imaging target are expected to contact the gantry front part 103. Note that as the contact detection unit 106, any device which can detect contact can be used. For example, it is possible to use an existing component such as a mechanical switch which is energized when a pressure is applied, touch pad, or touch panel. In addition, since it can be expected that, for example, the temperature of a contact portion changes upon contacting an object, a sensor or the like which detects contact through a temperature can be used as the contact detection unit 106.

In addition, if a distance sensor is used as each contact detection unit 106, contact can be detected when the distance detected by each distance sensor becomes smaller than a predetermined threshold. It is therefore possible to use such a distance sensor as the contact detection unit 106 (contact detection sensor). If it is difficult to obtain physical contact, in particular, using such a distance sensor makes it possible to more clearly recognize that each region of the human body is placed at a predetermined position. As a distance sensor, for example, it is possible to use a general distance sensor such as an ultrasonic sensor or a distance sensor using infrared light. The necessity to provide the contact detection units 106 on the gantry front part 103 has been described above.

Figure 4A:
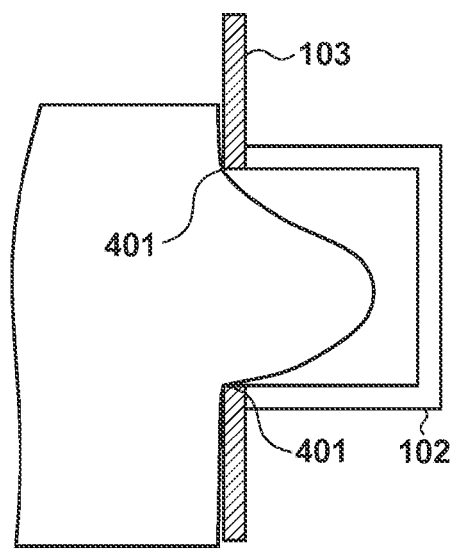
FIGS. 4A to 4C are views for explaining a gantry front part.
Figure 4C:
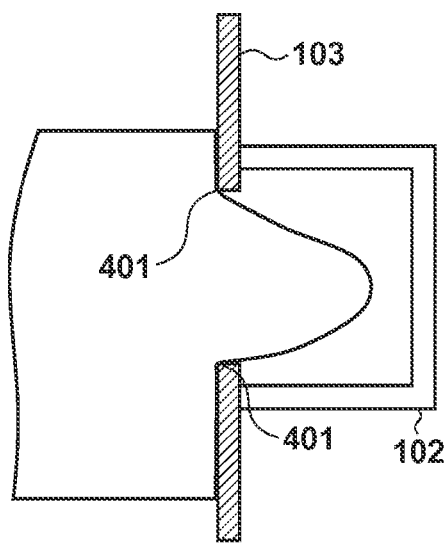
Figure 4B:
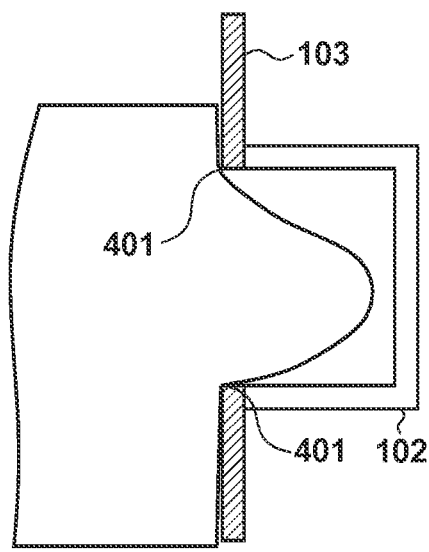

The placement of the contact detection units 106 (contact detection sensors) will be described next. The gantry front part 103 will be described first in more strictly. A material used for the gantry 100 has a finite thickness, and hence the structure shown in FIG. 4A or 4B can be provided as the structure of the gantry 100. Referring to FIG. 4A, the breast insert portion 102 does not contact peripheral portions of the breast. Referring to FIG. 4B, the edges of portions of the breast insert portion 102 are in contact with peripheral portions of the breast. In this case, at least in FIGS. 4A and 4B, since the portion indicated by the hatched portion can contact the periphery of the breast as an imaging target, at least the hatched portion is defined as the front part of the gantry (gantry front part 103). In the structure in FIG. 4C, a portion of the gantry front part 103 protrudes to the opening of the breast insert portion 102. In this case, since the protruding portion contacts the periphery of the breast as an imaging object, at least the hatched portion in FIG. 4C is defined as the gantry front part 103.

As described above, when the gantry front part 103, especially, a portion near the breast insert portion 102, is in contact with peripheral portions of the breast as an imaging target, the breast has been sufficiently deeply inserted. For this reason, the contact detection units 106 are preferably located near as possible to the breast insert portion 102. A portion near the boundary between the gantry 100 and the breast insert portion 102 (the boundary between the gantry front part 103 and the breast insert portion 102 in this embodiment) or a portion 401 of an edge forming the opening of the breast insert portion 102 is especially a proper portion on which the contact detection unit 106 is to be provided. On the other hand, placing the contact detection unit 106 on a portion slightly far from the breast insert portion 102 (a portion slightly far from the above boundary or the edge of the opening) can acquire additional information concerning an optimal posture or information concerning imaging. Such an arrangement will be described below with reference to FIGS. 5A to 6B.

Figure 5A:
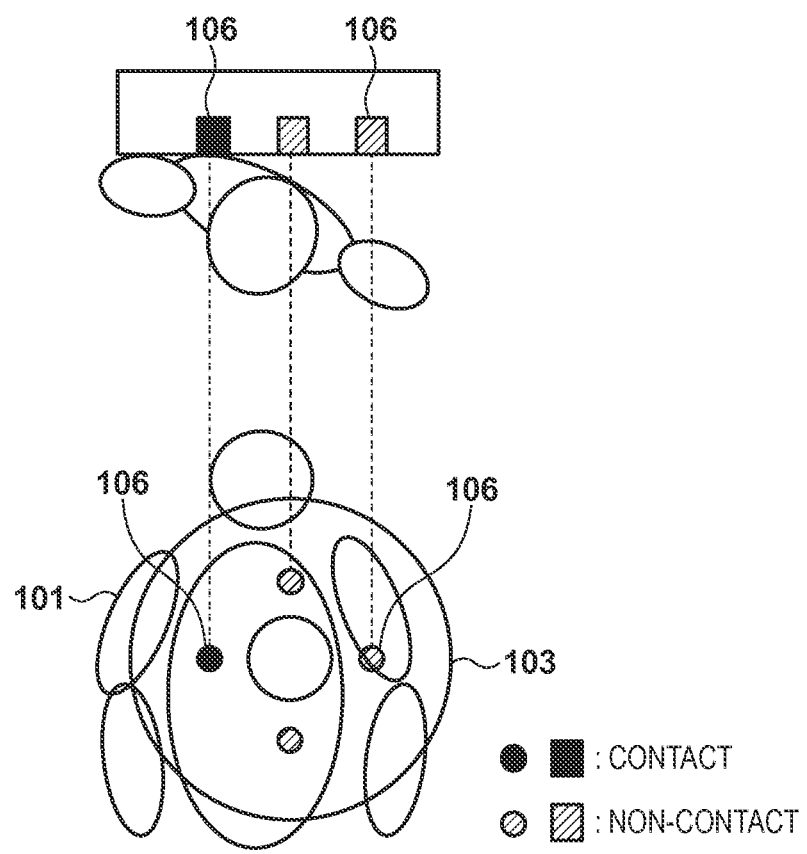
FIGS. 5A and 5B are views for explaining a detection method in a case in which an object and a gantry front part are nonparallel according to the first embodiment.
Figure 5B:
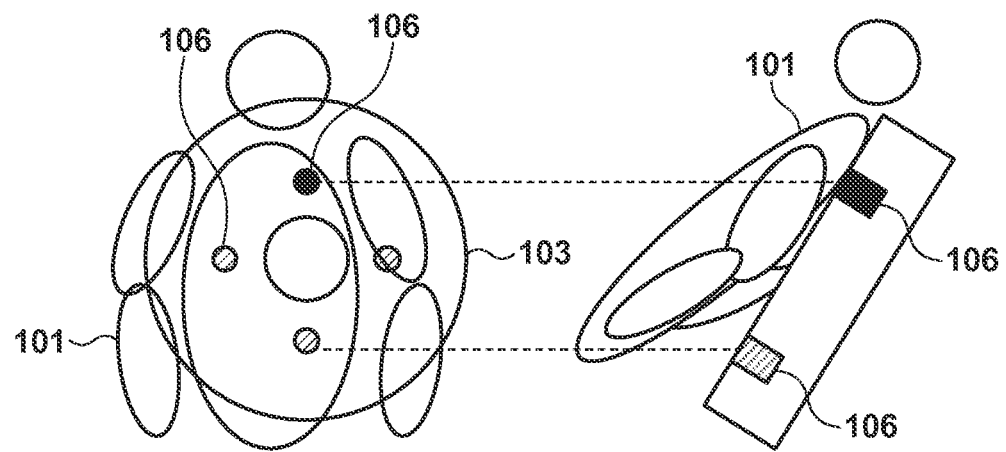

In order to image an object in a proper posture, the body of the object preferably faces the gantry front part in a parallel direction. For this reason, a plurality of contact detection sensors are preferably arranged and used. That is, it is preferable to detect the presence/absence of contact with the object at a plurality of positions on the gantry 100. For example, the posture of the object can be determined based on the distribution of information indicating the presence/absence of contact at a plurality of positions obtained from a plurality of contact detection sensors. A method of detecting a case in which the body of an object does not face the gantry front part in a parallel direction by using a plurality of contact detection sensors will be described with reference to FIGS. 5A and 5B. FIGS. 5A and 5B each exemplarily show a case in which the posture of the object is twisted with respect to the gantry front part 103, and the contact area between the body of the object and the gantry front part 103 is small.

In the case shown in FIG. 5A, only the contact detection unit 106, of the contact detection units 106 at the four positions, which is located on the left side of the object detects contact. Note that in this specification, this state will be referred to as the "posture twisted to the left". Likewise, the twisted state of the body of an object with the right side being nearer to the gantry front part 103 than the left side will be referred to as the "posture twisted to the right". The insert display unit 107 presents the operator with such a detected state obtained by the contact detection units 106 (the state in which only the contact detection unit 106 on the left side of the object detects contact). This presentation allows the operator to know that only the left side portion of the body of the object is in contact with the gantry front part 103. This makes it possible to instruct the object to make the right side portion of the body contact the gantry front part 103. This can insert the breast as an imaging target more deeply.

In the case shown in FIG. 5B, only the contact detection unit 106, of the contact detection units 106 at the four positions, which is located on the upper side of the object detects contact. Note that in this specification, this state will be referred to as the "posture leaning forward". When the body of the object leans backward, this posture is referred to as the "posture leaning backward". The insert display unit 107 presents the operator with such a detected state obtained by the contact detection units 106 (the state in which only the contact detection unit 106 on the upper side of the object detects contact). This presentation allows the operator to know that only the upper side portion of the body of the object is in contact with the gantry front part 103. This makes it possible to instruct the object to make also the lower side portion of the body contact the gantry front part 103. This can insert the breast as an imaging target more deeply.

Note that when detecting a combination of the states shown in FIGS. 5A and 5B, for example, the posture twisted to the left and leaning forward, it is possible to detect such a state by arranging the contact detection units 106 at upper left, upper right, lower left, and lower right positions on the gantry front part 103. That is, when only the contact detection unit 106 at the upper left position or only the contact detection units 106 at the upper left, left, and upper positions detect contact, it can be determined that the posture of the object is twisted to the left and is leaning forward. Alternatively, the above combination of states may be detected by expanding the detection range of each contact detection unit 106. In this case, for example, when the left contact detection unit 106 and the upper contact detection unit 106 detect contact, it can be determined that the posture is twisted to the left and is leaning forward.

As described above, the insert determination unit 205 can give a warning in accordance with which contact detection unit 106 has detected contact. For example, in the case shown in FIG. 5A, the insert determination unit 205 can warn to make the right portion of the body contact the gantry front part 103. In the case shown in FIG. 5B, the insert determination unit 205 can warn to make the lower portion of the body contact the gantry front part 103. Giving such a warning enables the operator to know that the breast has not been sufficiently deeply inserted and grasp a guideline for changing the posture of the object.

Figure 6A:
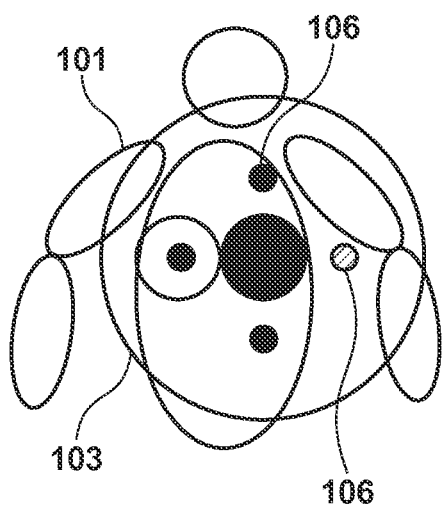
FIGS. 6A and 6B are views for explaining a method of determining the breast which is imaged according to the first embodiment.
Figure 6B:
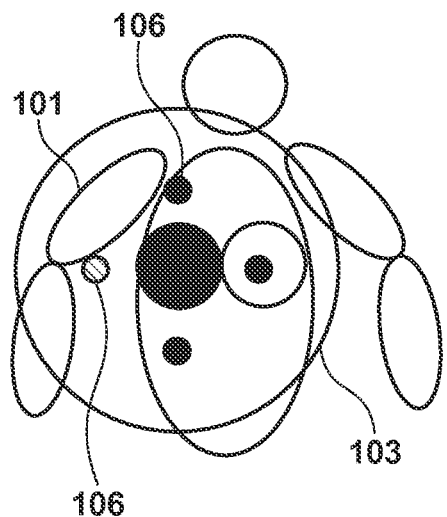

FIGS. 6A and 6B show a method of allowing the insert determination unit 205 to determine whether the breast which is imaged is the left or right breast, by grasping the contact state of each contact detection unit 106. In the cases shown in FIGS. 6A and 6B, it is determined, based on the distribution of information indicating the presence/absence of contact at a plurality of positions, which one of the left and right breasts of the object is inserted into the breast insert portion 102. FIG. 6A is a schematic view showing a case in which the right breast when seen from the object is imaged. In this case, the contact detection unit 106, of the left and right contact detection units 106, which is located on the right side when seen from the object detects no contact. In contrast to this, FIG. 6B is a schematic view showing a case in which the left breast when seen from the object is imaged. In this case, the contact detection unit 106, of the left and right contact detection units 106, which is located on the left side when seen from the object detects no contact. Therefore, the insert determination unit 205 can determine, from the detected state of contact by the contact detection unit 106, that the breast which is imaged is the left or right breast. In addition, whether the breast is sufficiently deeply inserted can be determined by checking whether all the contact detection units 106, other than the contact detection unit 106 which has detected no contact, have confirmed contact.

These left/right breast identifying methods often fail to identify when, for example, an arm of an object touches a contact detection unit. To cope with such a case, this apparatus may be separately provided with a mechanism with which the operator inputs information indicating the left or right breast. For example, when both the left and right contact detection units detect contact, the insert determination unit 205 determines a failure in identification, and accepts the designation of the left or right breast by the user. In addition, to detect that the arms are placed at correct positions, contact detection units may be provided at positions where the arms are placed such that the arms do not overlap the contact detection units used for determining the left and right breasts to be imaged. Arm contact detection units may be provided on the gantry side part 104 instead of the gantry front part 103. Furthermore, for example, such contact detection units provided to identify the left and right breasts may be provided so as to contact the breast which is not an imaging target.

Figure 7A:
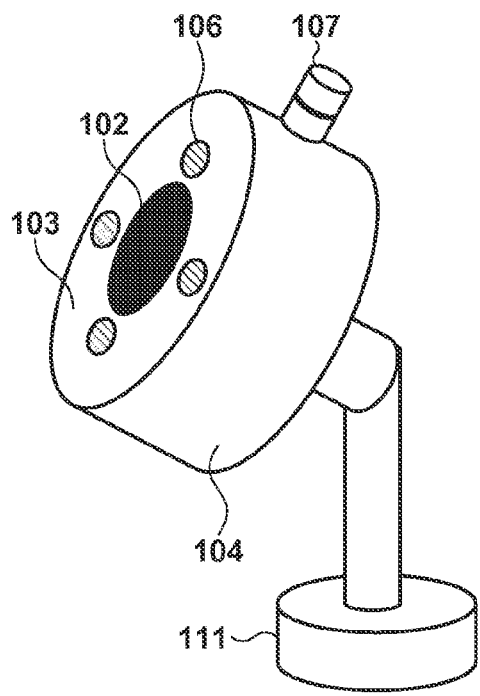
FIGS. 7A and 7B are perspective views for explaining a form of a contact detection unit according to the first embodiment.

Note that the contact detection units 106 shown in FIGS. 1A and 1B, 5A and 5B, and 6A and 6B are provided as a plurality of contact detection units in the manner shown in FIG. 7A. However, it is possible to use a contact detection unit capable of two-dimensional contact detection (a plurality of positions on the front part). In this case, the contact detection unit 106 can be arranged as shown in, for example, FIG. 7B. As the contact detection unit 106 in this case, for example, a touch pad or touch panel can be used. It is possible to determine the posture of an object or which one of the left and right breasts of the object is inserted into the breast insert portion, based on the distribution of information indicating the presence/absence of contact at a plurality of positions, which is obtained from the detection of two-dimensional contact. In addition, if a plurality of contact detection units 106 are provided, any unit of the plurality of contact detection units 106 which has not detected contact is displayed as a portion where no contact is made on the insert display unit 107 or the display device 109.

Figure 8A:
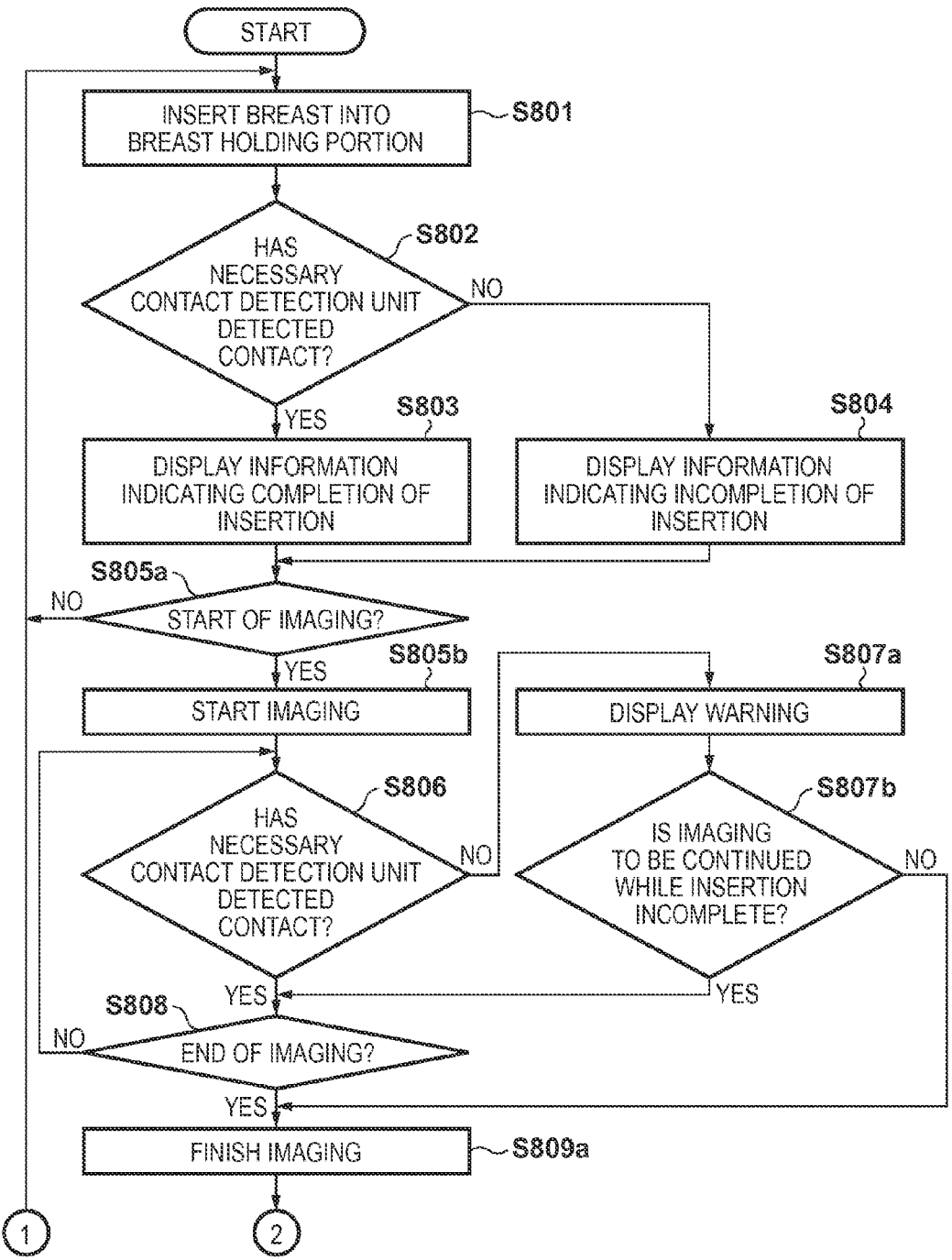
FIGS. 8A and 8B are flowcharts showing an example of a procedure in the breast tomography apparatus according to the first embodiment.
Figure 8B:
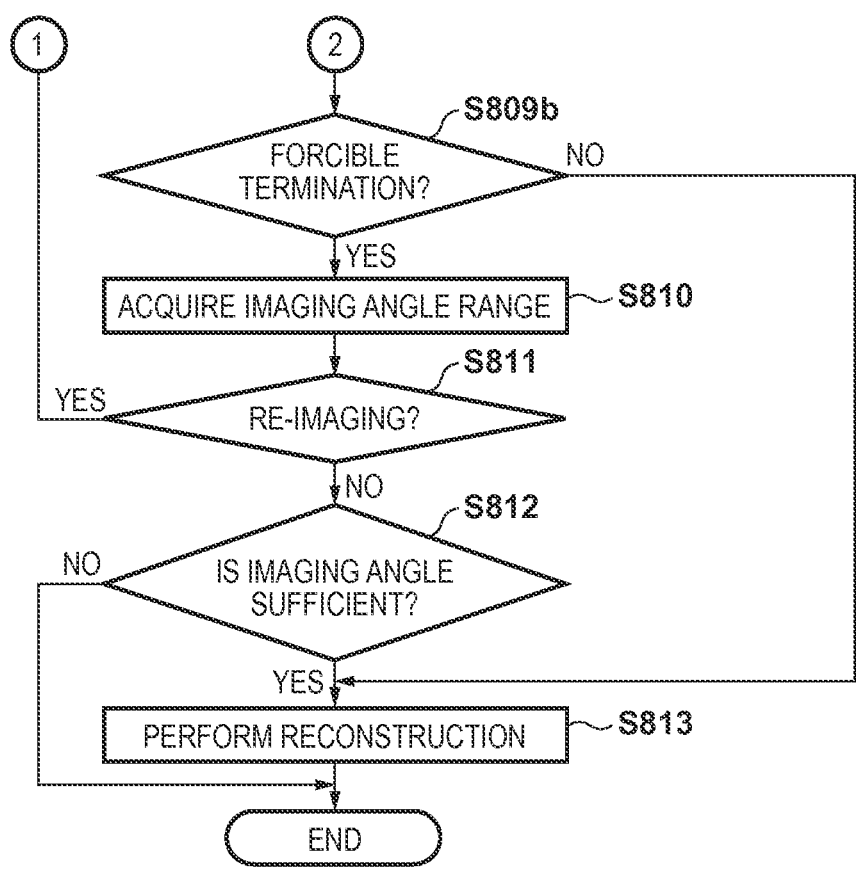

A procedure for processing in the first embodiment will be described next with reference to FIGS. 8A and 8B. First of all, in step S801, the breast as an imaging target of an object is inserted into the breast insert portion 102. As described above, when the breast as an imaging target is sufficiently deeply inserted, the contact detection units 106 attached to the gantry front part 103 detect contact with peripheral portions of the breast as an imaging target. In step S802, therefore, the insert determination unit 205 determines, based on the information sent from the contact detection units 106, whether all the contact detection units required to determine the completion of insertion are in contact with the human body.

In this case, the contact detection units required to determine the completion of insertion are contact detection units which should be in contact with an object when the object is in a proper posture. For example, all the contact detection units 106 provided immediately near the breast as an imaging target should detect contact when the object is in a proper posture, and hence are regarded as necessary contact detection units. On the other hand, as in the case shown in FIG. 6A, at the time of imaging the right breast when seen from the patient, the contact detection unit on the left side of the gantry front part 103 does not detect contact. Such a contact detection unit is not a necessary contact detection unit. The above definition of each contact detection unit required to determine the completion of insertion is held as information in the insert determination unit 205 in advance, and a necessary definition is read out in accordance with an imaging state.

If the contact determination result obtained in step S802 indicates that all the necessary contact detection units detect contact, the insert determination unit 205 displays information indicating the completion of insertion in step S803; otherwise, the insert determination unit 205 display information indicating the incompletion of insertion in step S804. Note that the insert display unit 107 or the display device 109 displays information indicating the completion of insertion or the incompletion of insertion, as the case may be. If the insert display unit 107 is formed from a lamp, settings are made to cause the lamp to emit red light at the time of the incompletion of insertion and emit green light at the time of the completion of insertion. If the insert display unit 107 is formed from a display or the like, the unit displays messages corresponding to determination results indicating the completion or incompletion of insertion, respectively. The display device 109 also performs similar display concerning determination results indicating the completion or incompletion of insertion. In addition, a guideline concerning the correction of a body posture may be displayed on the insert display unit 107 or the display device 109.

When an instruction to start imaging is issued in step S805*a*, the process advances to step S805*b*, in which the insert determination unit 205 instructs the apparatus control unit 204 to start imaging. That is, the insert determination unit 205 causes the radiation source 201 to start applying radiation, and also causes the apparatus control unit 204 to start rotating the arm 203 to start the acquisition of a projection image by the radiation detector 202. If there is no instruction to start imaging, the process returns to step S801. Note that in FIGS. 8A and 8B, an instruction to start imaging is accepted regardless of whether insertion is complete. However, the present invention is not limited to this. For example, after information indicating the incompletion of insertion is displayed in step S804, the process may return to step S801 so as to inhibit the acceptance of an operation to start a normal imaging operation. In this case, it is preferable to separately define an operation for forcibly starting imaging without confirmation of the completion of insertion.

In step S806, the insert determination unit 205 determines whether the necessary contact detection units continue the detection of contact during imaging. If the necessary contact detection units cannot detect contact, it indicates that contact is lost by the body motion or the like of an object during imaging. The process therefore advances to step S807a, in which the insert determination unit 205 presents a warning message of the incompletion of insertion by using the display device 109 or the insert display unit 107. In step S807b, the insert determination unit 205 determines whether imaging is to be continued in the state of the incompletion of insertion. If imaging is not to be continued in the state of the incompletion of insertion, the process advances to step S809a, in which the insert determination unit 205 instructs the apparatus control unit 204 to stop imaging, and finishes imaging. If it is determined in step S807b that imaging is to be continued even in the state of the incompletion of insertion, the process advances to step S808.

Note that the user may be made to make settings in advance whether to continue or forcibly finish imaging when the incompletion of insertion is determined during imaging. Alternatively, the user may be made to issue an instruction to determine in step S807b whether to forcibly finish imaging. In this case, the user can select whether to continue imaging after the generation of a warning against the incompletion of insertion. If there are a plurality of contact detection units 106, more detailed conditions concerning the execution/non-execution of forcible termination may be separately set. For example, it is possible to set conditions for determination in step S807 such that forcible termination is performed only when all the sensors detect no contact, and imaging is continued when at least one sensor detects contact. Alternatively, for example, conditions may be set such that forcible termination is performed when a sensor immediately near the breast as an imaging target detects no contact, and imaging is continued while a warning is displayed when a sensor immediately near the breast detects contact but a sensor for detecting, for example, the twisted posture of the body like that shown in FIG. 5A or 5B detects no contact.

In step S808, the insert determination unit 205 determines the end of imaging when the user issues an instruction to finish imaging or the arm 203 has rotated through an angle necessary for tomography. Upon determining the end of imaging, the insert determination unit 205 instructs the apparatus control unit 204 to stop imaging, and finishes imaging in step S809a. Note that in the processing in steps S801 to S809a up to the end of imaging described above, the insert determination unit 205 always monitors the detection of contact in real time. In step S809b, the insert determination unit 205 determines whether the end of imaging which is executed in step S809a is determined based on the completion of an imaging operation or forcible termination.

If the end of imaging is not based on forcible termination (is based on the completion of the imaging operation), it indicates that data necessary for reconstruction have been sufficiently acquired. The process therefore advances to step S813, in which the image processing unit 206 executes reconstruction to generate a tomographic image.

Upon determining forcible termination in step S809b, the insert determination unit 205 acquires an imaging angle range from the apparatus control unit 204 in step S810. The imaging angle range is obtained by causing the apparatus control unit 204 to acquire an imaging angle at the time of forcible termination. In step S811, the insert determination unit 205 receives an instruction concerning the execution/non-execution of re-imaging from an operator such as a radiological technician. At this time, the insert determination unit 205 may display, on the display device 109, the imaging angle range acquired in step S810 or a determination result indicating whether reconstruction can be performed within the imaging angle range. Note that the image processing unit 206 determines whether re-imaging can be performed.

If an instruction not to execute re-imaging is received from the operator, the process advances to step S812. Upon determining that re-imaging can be performed, the image processing unit 206 performs reconstruction in step S813. Upon determining that reconstruction cannot be performed, the image processing unit 206 finishes imaging without performing reconstruction. When performing reconstruction in step S813, the image processing unit 206 determines, based on the imaging angle range acquired in step S810, whether an obtained projection images are used for reconstruction, and performs reconstruction by using only minimum necessary images. This makes it possible to perform reconstruction with little motion artifacts.

As described above, according to the breast tomography apparatus of the first embodiment, it is possible to accurately check that the breast is sufficiently deeply inserted, regardless of the size of the breast, and to detect the motion of the human body with a less storage capacity using a simple method. That is, the first embodiment is configured to determine the insert condition of the breast by checking contact between peripheral portions of the breast and the gantry front part 103, and hence can accurately check the insertion of the breast, independently of the size of the breast, as compared with the method disclosed in patent literature 1. In addition, it is not necessary to perform radiography for checking insertion. This can reduce the exposure dose of radiation as compared with the method disclosed in patent literature 2.

<Second Embodiment>

The first embodiment is configured to determine the insert condition of the breast into the breast insert portion 102 based on the presence/absence of contact between the breast and the gantry front part 103. The second embodiment is configured to check the intensity or dispersion of contact between the breast and a gantry front part 103 by using contact detection units 106 which can determine not only the presence/absence of contact but also the pressure of contact. The second embodiment is configured to detect, for example, the pressures of contact from an object at a plurality of positions and determine the insert condition of the breast into a breast insert portion 102 based on the dispersion of pressures and/or the average value of the pressures at the plurality of positions. This makes it possible to more accurately observe the motion of the object and more accurately determine the insert condition of the breast and the permission/inhibition of imaging. Although the arrangement of a breast tomography apparatus according to the second embodiment is the same as that according to the first embodiment (FIGS. 1A to 2), a contact detection sensor capable of determining not only the presence/absence of contact but also the pressure of contact is used as each contact detection unit 106, as described above.

Figure 2:
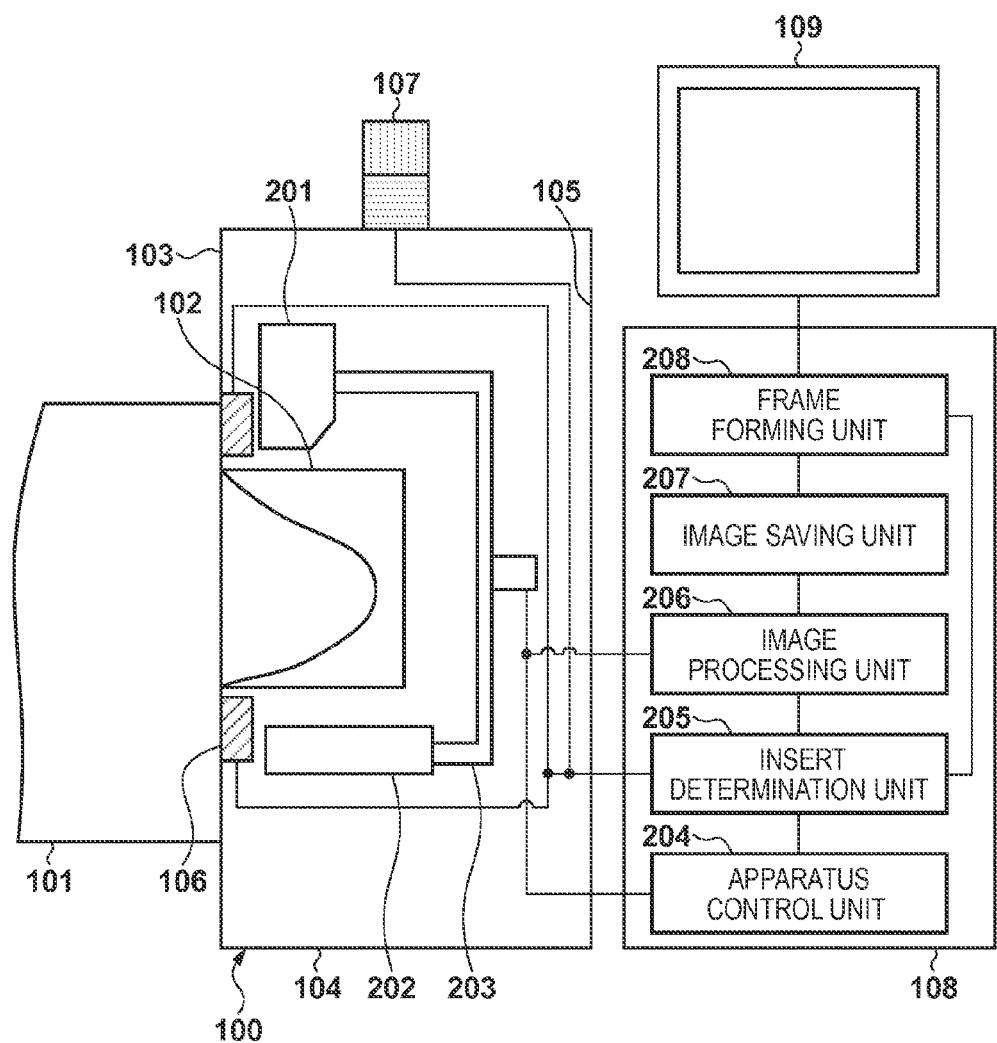
FIG. 2 is a view showing an example of the schematic arrangement of the breast tomography apparatus according to the first embodiment.
Figure 7B:
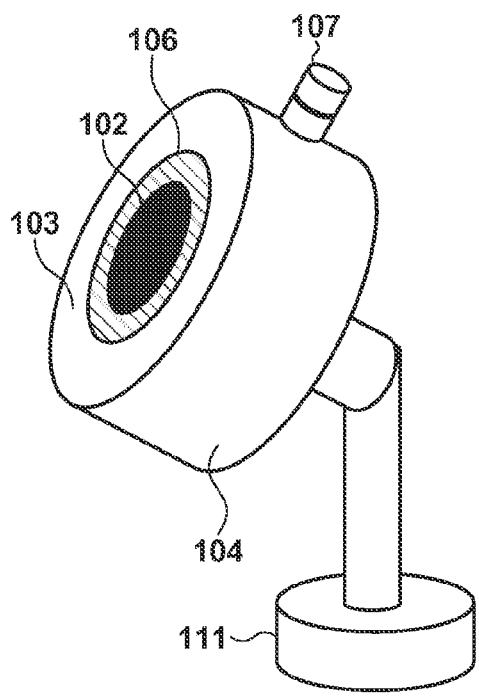

A plurality of sensors capable of determining the pressures of contact are provided in the same manner as shown in FIGS. 1A to 2. Providing a plurality of sensors can obtain not only the average value of pressure values obtained from all the sensors but also the dispersion of pressure values (for example, differences from an average value or a standard deviation). In addition, if the contact detection unit 106 is formed from one contact detection sensor as shown in FIG. 7B, assume that the single contact detection sensor can present the distribution or dispersion of pressures. Assume that an insert determination unit 205 calculates a dispersion such as a standard deviation. In this embodiment, the insert determination unit 205 performs this calculation by using a processor and a storage device in a computer 108.

In addition, in this embodiment, a portion with a detected pressure lower than a predetermined threshold is displayed as a portion with weak contact on an insert display unit 107 or a display device 109. When displaying on the insert display unit 107 or the display device 109, it is possible to provide a plurality of thresholds and make the insert display unit or the display device change the color to be displayed for each of the different thresholds. In addition, such a threshold may be set for the contact detection unit 106 at each position.

Figure 9:
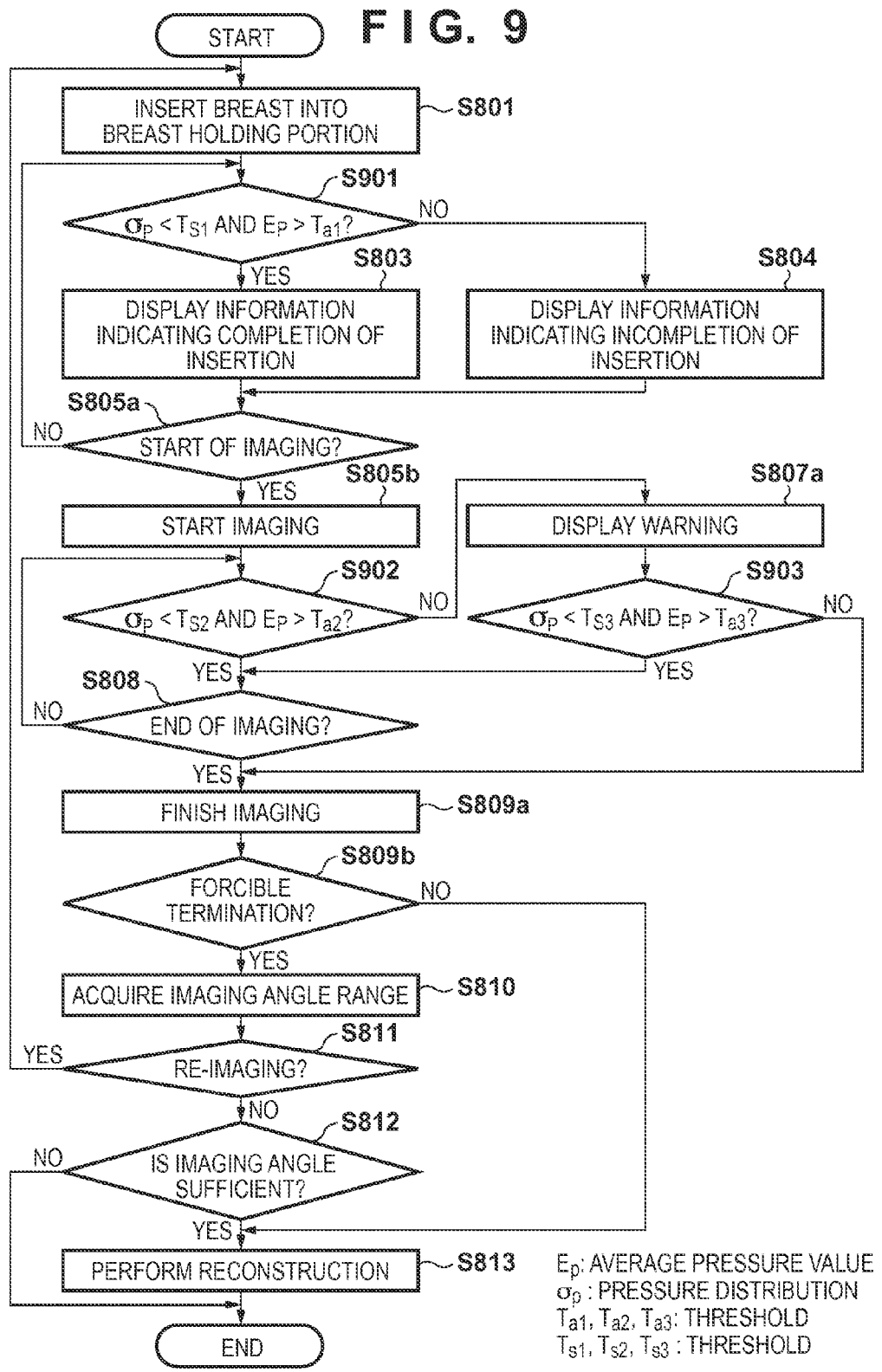
FIG. 9 is a flowchart showing an example of a procedure in a breast tomography apparatus according to the second embodiment.

The operation of the breast tomography apparatus according to the second embodiment will be described next with reference to the flowchart of FIG. 9. Note that in the following case, the completion of insertion and the incompletion of insertion are determined based on the average value and standard deviation of pressures. The same step numbers as those in the first embodiment (FIGS. 8A and 8B) denote the same processing steps in the flowchart of FIG. 9.

As in the first embodiment, after the insertion of the breast, the insert determination unit 205 performs insert determination in step S901. In the first embodiment, the completion of insertion is determined based on the presence/absence of contact detected by the contact detection units 106. In the second embodiment, this determination is performed based on pressure values from the plurality of contact detection units 106. That is, when an average value $E_p$ of pressure values exceeds a threshold $T_{a1}$ and the dispersion (standard deviation $\sigma_p$) of a pressure distribution becomes smaller than a threshold $T_{S1}$, it is determined that insertion is complete. The process then advances to step S803. Although the standard deviation is used as the dispersion of the pressure distribution, any quantity that represents the dispersion can be used.

The standard deviation is derived from the pressure of contact from each sensor and the average of the pressures of contact from all the sensors. Assume that there are four contact detection units as shown in FIGS. 1A and 1B. In this case, letting $p_i$ (i=1, 2, 3, 4) be the value of each sensor, an average value $E_p$ is obtained by $$\sigma = \sqrt{\frac{1}{N}\sum_{i=1}^{N}(p_i - E_p)^2} \quad (1)$$

$$E_p = \frac{1}{N}\sum_{i=1}^{N} p_i$$

Likewise, in determination on the completion of insertion/incompletion of insertion in steps S902 and S903, the average value $E_p$ and the standard deviation $\sigma_p$ are obtained and compared with thresholds $T_{a2}$, $T_{S2}$, $T_{a3}$, and $T_{S3}$ to perform contact determination. Other processes are the same as those in the first embodiment. Obviously, the second embodiment can also be applied to both a sitting posture type breast tomography apparatus and a prone posture type breast tomography apparatus. In addition, the thresholds $T_{a3}$ and $T_{S3}$ in step S903 are allowable values for the continuation of imaging even if the incompletion of insertion is determined. The operator may set the thresholds $T_{a3}$ and $T_{S3}$ to arbitrary values.

Merits in performing contact determination by obtaining an average value and a standard deviation will be described below. When an object is in a stable posture, a uniform force having a certain magnitude is applied to each of a plurality of contact detection units. When an object is in an instable posture, nonuniform forces are applied to the plurality of contact detection units. For example, when a large pressure is detected by a contact detection unit, of the contact detection units, which is located on an upper portion, it indicates that the posture is slightly leaning forward. Therefore, when the dispersion of the pressure values obtained from the contact detection units 106 is large, it indicates that the posture is instable, which is a state unsuitable for imaging. According to the second embodiment, it is possible to accurately determine whether the posture is stable, by checking the distribution of contact pressures. This makes it possible to prevent misshooting more effectively than the first embodiment.

<Third Embodiment>

In the first and second embodiments, the contact detection units 106 are arranged on the gantry front part 103 to determine the insert condition of the breast into the breast insert portion 102. In the third embodiment, an illuminance detection sensor is provided in a breast insert portion 102 to determine the insert condition of the breast into the breast insert portion 102 based on the detected illuminance. The third embodiment provides an arrangement which can determine an insert condition with a simpler arrangement than that in the first and second embodiments.

Figure 10:
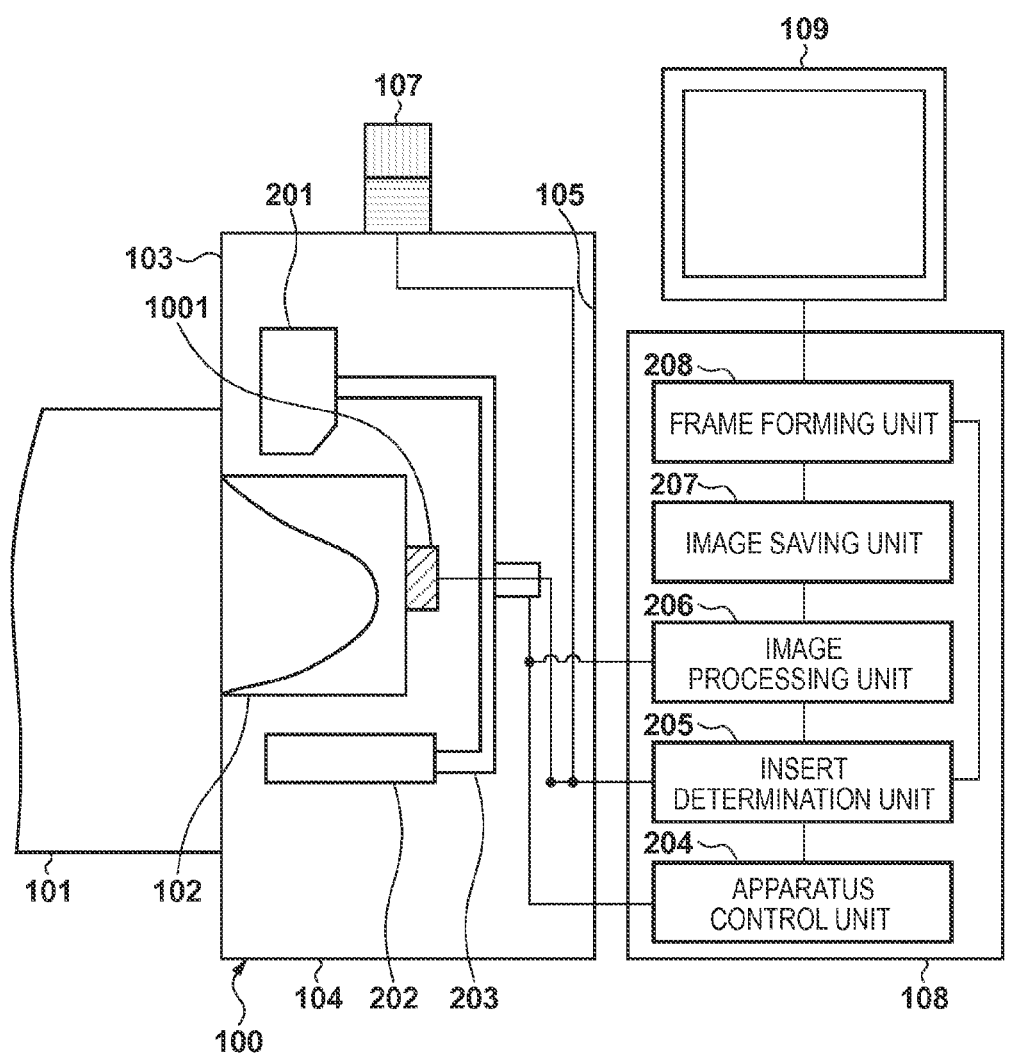
FIG. 10 is a view showing an example of the schematic arrangement of a breast tomography apparatus according to the third embodiment.

The arrangement of a breast tomography apparatus according to the third embodiment is the same as that according to the first embodiment (FIGS. 1A to 2) except that the contact detection unit 106 does not exist, and an illuminance detection unit 1001 which measures illuminance (the intensity of light) is provided in the breast insert portion 102, as shown in FIG. 10. In general, the breast tomography apparatus is installed in a room with bright illumination. For this reason, the interior of the breast insert portion 102 has a certain illuminance because of the illumination in the room while the breast is not inserted, whereas the interior of the breast insert portion 102 becomes dark and has a low illuminance after the breast is inserted into the breast insert portion 102 because the breast insert portion is covered with the breast as an imaging target. The breast tomography apparatus according to the third embodiment has the illuminance detection unit 1001 provided in the breast insert portion 102 to detect the insertion/non-insertion of the breast by monitoring the illuminance of the interior.

Note that the illuminance detection unit 1001 is an illuminance detection sensor. As the illuminance detection unit 1001, a device which detects light, such as a photodiode or image sensor, is used.

The placement position of the illuminance detection unit 1001 will be described with reference to FIGS. 12A and 12B. When one illuminance detection unit 1001 is to be used, it is placed in the center of the bottom surface of the breast insert portion 102 as shown in FIG. 12A. With this placement, the illuminance detection unit 1001 exhibits weak sensitivity to light at a portion where light tends to leak, that is, light near the boundary between the breast insert portion 102 and a gantry front part 103. If, therefore, it is possible to provide a plurality of illuminance detection units 1001, a plurality of illuminance detection units 1001 are provided near the boundary between the breast insert portion 102 and the gantry front part 103 as shown in, for example, FIG. 12B. This makes it possible to more accurately detect changes in illuminance near the boundary.

The operation of the breast tomography apparatus according to the third embodiment will be described next with reference to the flowchart of FIG. 11. Note that the same step numbers as those in the first embodiment (FIGS. 8A and 8B) denote the same processing steps in the flowchart of FIG. 11. In the first embodiment, the completion of insertion is determined in steps S802 and S806. In the third embodiment, instead of this processing, the completion/incompletion of insertion is determined in steps S1101 and S1102 based on illuminance in the breast insert portion.

In step S801, an insert determination unit 205 keeps monitoring the illuminance in the breast insert portion 102 by using the illuminance detection unit 1001 during the insertion of the breast, and compares the detected illuminance with a threshold, thereby determining the insert condition of the breast into the breast insert portion 102. If, for example, an illuminance $E_L$ becomes less than a threshold $T_L$, information indicating the completion of insertion is displayed in step S803; otherwise, information indicating the incompletion of insertion is displayed in step S804. Even after imaging is started in step S805b, the insert determination unit 205 keeps incessantly monitoring the illuminance in the breast insert portion 102 in step S1102. If the illuminance $E_L$ is equal to or more than the threshold $T_L$, the insert determination unit 205 displays a warning in step S807a. In this case, it is possible to forcibly terminate imaging as in the first embodiment.

Figure 11:
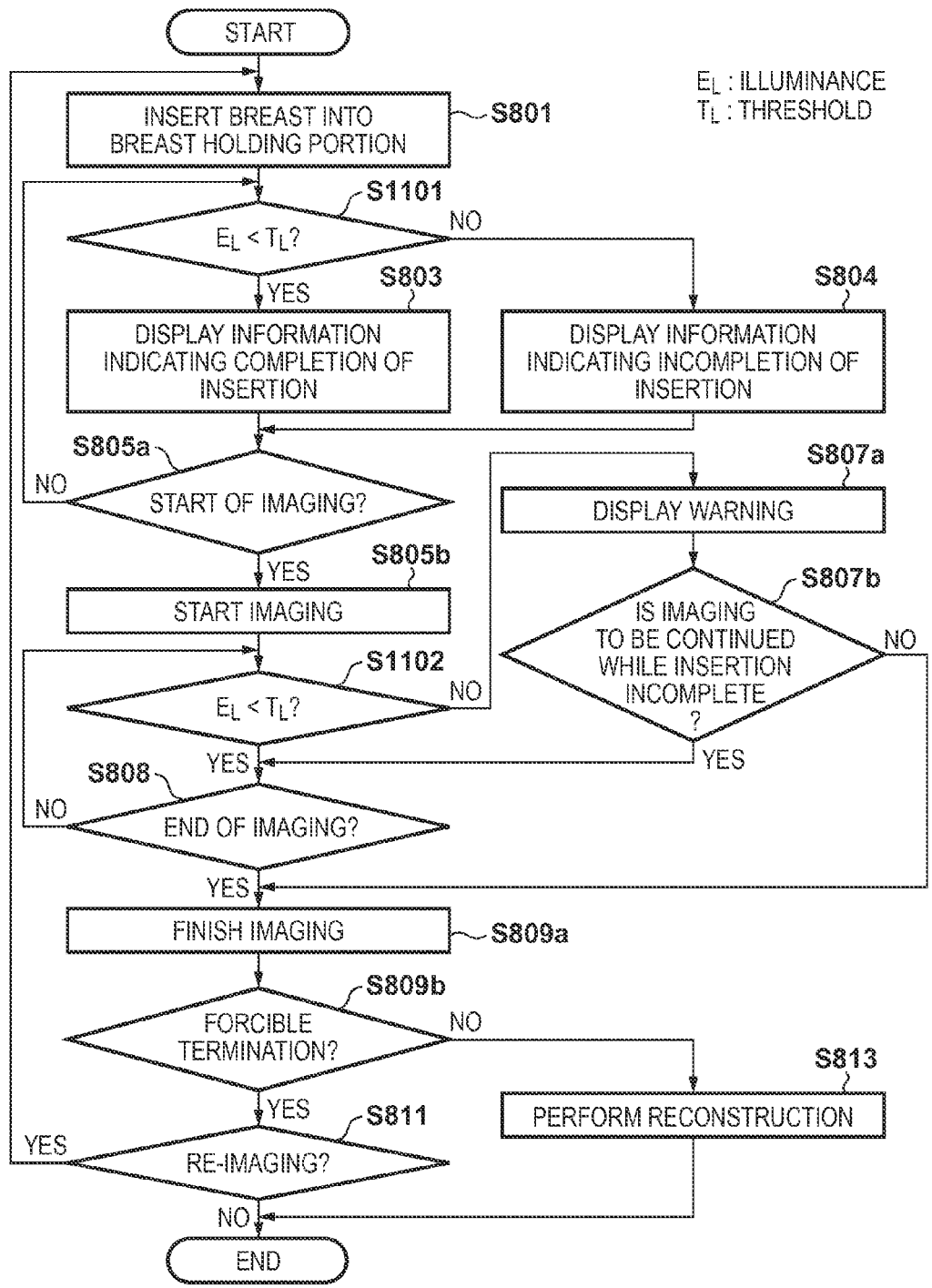
FIG. 11 is a flowchart showing an example of a procedure in the breast tomography apparatus according to the third embodiment.

Although in the flowchart of FIG. 11, the acquisition of an imaging angle range and imaging angle determination respectively performed in steps S810 and S812 are skipped, it is possible to execute these processes in the same manner as in the first embodiment. This is because an imaging angle range can be obtained by recording the time when the illuminance has increased (that is, the breast has come off). In addition, as in the first embodiment, it is obvious that images to be used for reconstruction in step S813 can be determined. Furthermore, obviously, the third embodiment can be applied to both a sitting posture type breast tomography apparatus and a prone posture type breast tomography apparatus.

The third embodiment is advantageous over the first and second embodiments in that it is possible to detect the insertion of the breast by using at least one sensor. On the other hand, the first and second embodiments are advantageous over the third embodiment in terms of the reliability of detection because a low illuminance does not necessarily indicates that the breast is inserted to a sufficient depth when, for example, the illumination is dark.

<Fourth Embodiment>

In the fourth embodiment, a breast tomography apparatus equipped with a breast suction mechanism like that described in patent literature 3 determines the insert condition of the breast into a breast insert portion 102 based on the air pressure in the breast insert portion 102. When the breast as an imaging target is inserted into the breast insert portion 102, the breast insert portion 102 is hermetically closed by the inserted breast, and the air pressure in the breast insert portion 102 decreases. Detecting a decrease in air pressure can detect the insertion/non-insertion of the breast.

FIG. 13 shows the arrangement of the fourth embodiment. The arrangement of the breast tomography apparatus according to the fourth embodiment is the same as that according to the first embodiment (FIGS. 1A to 2) except that an air pressure detection unit 1301 is provided instead of the contact detection unit 106. That is, this apparatus includes the air pressure detection unit 1301 which detects the air pressure in the breast insert portion 102 and a pump 1302 as a suction mechanism for decompressing the breast insert portion 102. The breast insert portion 102 is hermetically closed by the breast properly inserted into the breast insert portion 102 and can be held in a vacuum state.

Note that an insert determination unit 205 includes a timer for measuring the elapsed time since the start of the operation of the vacuum pump. This timer may be implemented by software using a computer or hardware. Other arrangements are the same as those in the first and second embodiments.

The operation of the breast tomography apparatus according to the fourth embodiment will be described with reference to the flowchart of FIG. 14. Note that the same step numbers as those in the first embodiment (FIGS. 8A and 8B) denote the same processing steps in the flowchart of FIG. 14. After the insertion of the breast in step S801, an operator such as a radiological technician issues an instruction to start suction by using a display device 109 also functioning as an input device. When the operator issues an instruction to start suction, the pump 1302 starts to operate in step S1401, and evacuates (decompresses) the interior of the breast insert portion 102.

When an object is properly in contact with the gantry front part, since the breast insert portion 102 is hermetically closed by the breast as an imaging target, the air pressure in the breast insert portion 102 decreases. In steps S1402 and S1403, it is determined whether the air pressure in the breast insert portion 102 has become equal to or less than a threshold within a predetermined time from the start of the operation of the pump. The insert condition of the breast is then determined based on this determination. In step S1402, the insert determination unit 205 keeps monitoring a decrease in air pressure in the breast insert portion 102 by using the air pressure detection unit 1301. Note that the state of air pressure in the breast insert portion 102 is displayed in real time on an insert display unit 107 or the display device 109. The operator can sequentially observe whether decompression is properly performed during suction, by checking the vacuum state (air pressure) in the breast insert portion 102 which is displayed in real time.

If the air pressure has decreased lower than a predetermined threshold $P_0$ within a predetermined time $T_0$, the insert determination unit 205 determines that suction has been sufficiently performed, that is, insertion is complete (steps S1402 and S1403). In this case, the process advances to step S1404, in which the insert determination unit 205 stops suction using the pump 1302, and displays information indicating the completion of suction and/or the completion of insertion on the insert display unit 107 or the display device 109. On the other hand, if the air pressure has not decreased lower than the threshold $P_0$ after the lapse of the predetermined time $T_0$, it indicates that the breast insert portion 102 is not hermetically closed, and hence the object is not properly in contact with the gantry front part 103. That is, if the air pressure has not decreased even after the lapse of the predetermined time $T_0$ while the elapsed time since the start of suction is monitored, the insert determination unit 205 stops suction and displays information indicating the incompletion of suction and/or the incompletion of insertion on the insert display unit 107 or the display device 109 (step S1405).

Even after the start of imaging, the insert determination unit 205 keeps monitoring the air pressure in the breast insert portion 102 in step S1406. If the air pressure becomes equal to or more than $P_0$ during this monitoring operation, it is known that air has externally entered the breast insert portion 102. This indicates that the breast as an imaging target has come off the breast insert portion 102, and the hermetic state cannot be maintained. In this case, the process advances to step S807a, in which the insert determination unit 205 displays a warning. In step S807b, the insert determination unit 205 determines whether to continue imaging.

Note that when the object leans backward to separate the body from a gantry front part 103, the volume of the breast insert portion 102 which is occupied by the breast decreases while the breast is fixed to the apparatus. Consequently, the volume of the void in the breast insert portion 102 increases. For this reason, the pressure in the breast insert portion 102 further decreases lower than that at the start of imaging. In order to monitor this, the pressure value from the air pressure detection unit 1301 is compared with a lower limit value $P_1$ in step S1406. When the pressure in the breast insert portion 102 becomes lower than the lower limit value $P_1$, the process also advances to step S807a.

Obviously, the fourth embodiment can be applied to both a sitting posture type breast tomography apparatus and a prone posture type breast tomography apparatus. Although in the flowchart of FIG. 14, the processes in steps S810 and S812 are skipped, it is obvious that similar processes can also be executed in the fourth embodiment.

As described above, the fourth embodiment has the advantage of being capable of determining the insert condition of the breast by using one sensor. In addition, this embodiment has another advantage that the placement of the air pressure detection unit 1301 is not limited as long as it is provided in the breast insert portion 102. Note however that the fourth embodiment cannot be used without a suction device such as a vacuum pump.

<Fifth Embodiment>

The first to fourth embodiments use the detection of physical quantities (the presence/absence of contact, the pressure of contact, illuminance, and air pressure). The fifth embodiment will exemplify an arrangement configured to determine the insert condition of the breast without providing any contact detection unit or the like. More specifically, the fifth embodiment will exemplify an arrangement configured to check the degree of insertion of the breast by obtaining in advance a radiographic image of the breast before tomography (an image obtained at this time is called a previous image). This embodiment will also exemplify an arrangement configured to sequentially check the degree of insertion of the breast by comparing portions of images which include no imaging target during tomography.

FIG. 15 shows the arrangement of the fifth embodiment. The arrangement of a breast tomography apparatus according to the fifth embodiment is the same as that according to the first embodiment (FIGS. 1A to 2) except that the contact detection unit 106 is not provided. An insert determination unit 205 according to the fifth embodiment continuously determines the insert condition of the breast by detecting the insert condition of the breast into a breast insert portion 102 from a previous image before the start of imaging, counting the number of direct irradiated pixels, and comparing the counted number with the number of direct irradiated pixels on a previously obtained image.

Note that as in the first embodiment, the determination result (completion of insertion/incompletion of insertion) on the insert condition obtained by the insert determination unit 205 is displayed on an insert display unit 107 or a display device 109, and the operator determines the insert condition of the breast based on the information displayed on the insert display unit 107 or the display device 109. In addition to this, in the fifth embodiment, a previous image and an image during tomography are displayed on the display device 109 or the like. The operator can determine, based on these pieces of displayed information, whether the breast has been properly inserted.

Figure 16B:
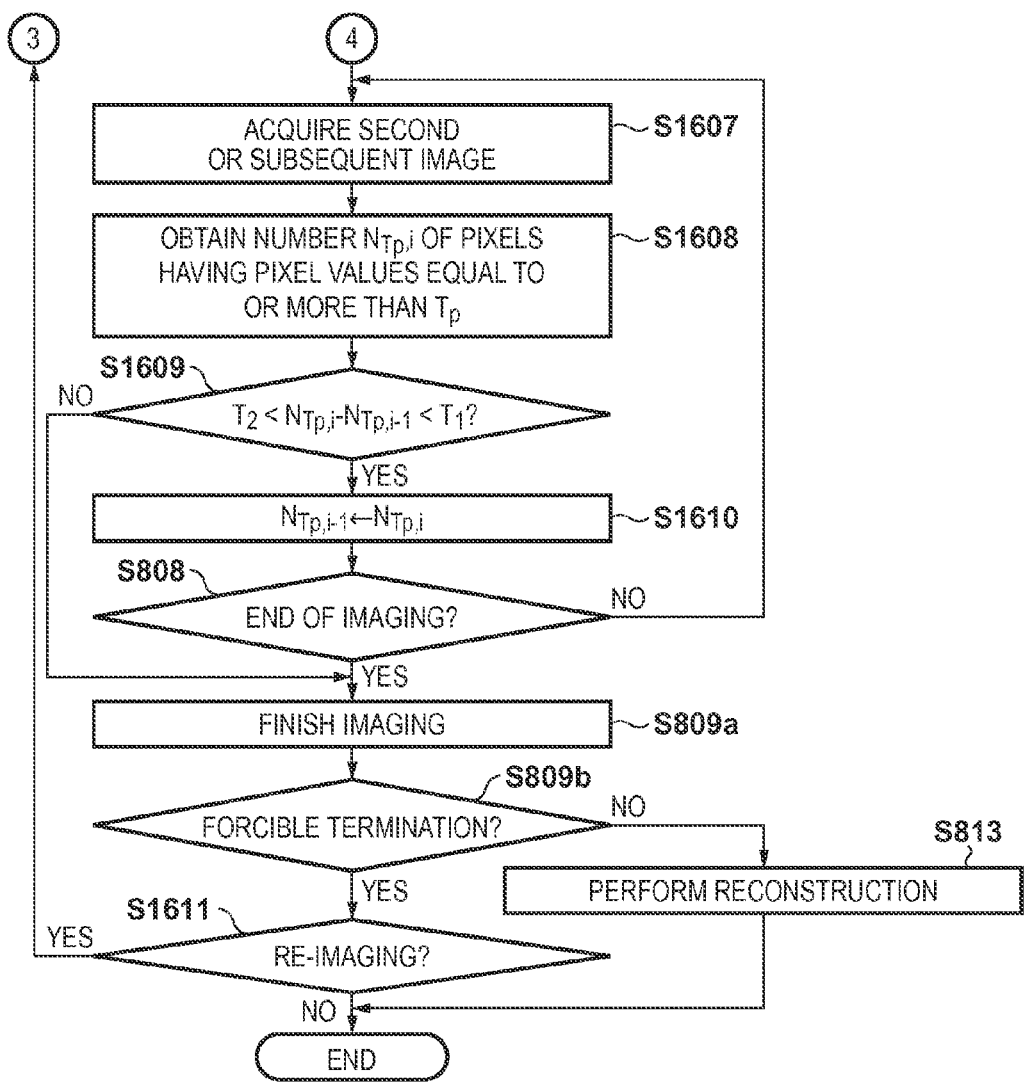

The operation of the breast tomography apparatus according to the fifth embodiment will be described next with reference to the flowchart of FIGS. 16A and 16B. The same step numbers as those in the first embodiment (FIGS. 8A and 8B) denote the same processing steps in the flowchart of FIGS. 16A and 16B. After the insertion of the breast in step S801, it is determined in step S1601 whether to start pre-imaging for checking the insert condition of the breast. Assume that the operator has issued an instruction to start pre-imaging. Imaging to be performed to acquire one or more images for alignment or the like before tomography is called scout imaging. For example, Japanese Patent Laid-Open No. 2012-130542 (to be referred to as patent literature 4 hereinafter) discloses a technique of performing imaging as scout imaging from two directions, namely the AP direction and lateral direction of an object.

When an instruction to start pre-imaging is issued, the insert determination unit 205 acquires at least two previous images including a radiographic image from the first direction and a radiographic image from the second direction (preferably a direction perpendicular to the first direction) different from the first direction. In this embodiment, the insert determination unit 205 acquires a radiographic image by applying radiation from up to down using an apparatus control unit 204 in step S1602. In step S1603, the insert determination unit 205 acquires an image by applying radiation from right to left after an arm 203 is rotated through 90° using the apparatus control unit 204. Obviously, radiation may be applied from down to up and from left to right. Note that the definitions of "up", "down", "right", and "left" follow those made in FIGS. 1A and 1B.

Subsequently, in step S1604, the two obtained previous images are displayed on the display device 109. When displaying the previous images, an image processing unit 206 performs image processing such as offset correction, gain correction, defect correction, and tone processing, as needed. An operator such as a radiological technician can check the insert condition of the breast as an imaging target in the lateral direction by checking the previous image acquired by applying radiation from up to down. Likewise, the operator can check the insert condition of the breast as an imaging target in the vertical direction by checking the previous image acquired by applying radiation from right to left.

In pre-imaging described above, it is possible to more accurately perform position determination by acquiring two images from different angles than by acquiring one image. Consider a state in which an object leans forward as shown in FIG. 17A. In this case, when imaging is performed under only one condition: that radiation be applied only from up to down (corresponding to FIG. 17B), the breast looks smaller in size than when the breast is in a proper posture. In other respects, however, it is difficult to discriminate them. FIG. 17B is a schematic view showing the image obtained when radiation is applied from up to down.

FIG. 17C shows the image obtained when radiation is also applied from right to left. When radiation is also applied from right to left, it is possible to easily recognize a partial loss near the chest wall, as indicated by a loss portion 1703. This makes it possible to easily discriminate that the object is in a posture leaning forward. Likewise, when only the right and left sides of the body of the object are in contact, it is possible to discriminate such a case by the image (FIG. 17B) obtained when radiation is applied from up to down.

Note that with regard to irradiation directions of radiation, radiation is applied from up to down and from right to left in the above embodiment. In general, however, similar effects can be expected by performing imaging from two directions whose angles differ in angle to some extent. Note however that the operator can more easily recognize an imaging state when using, as irradiation directions, the up-to-down direction (the body axis direction of the object) and the left-to-right direction (a direction perpendicular to the body axis of the object) than when applying radiation from other directions. For this reason, it is preferable to display previous images when radiation is applied in the up-to-down direction and the left-to-right direction. In addition, according to the above description, the two directions differ by an angle of 90°. However, the present invention is not limited to this. For example, similar effects can be expected even when performing imaging at angles that allow discrimination of the insertion/non-insertion of the breast, for example, at angles that differ by 85°.

In addition, it is possible to obtain three or more images as previous images. However, as the number of obtained images increases, the exposure dose of radiation on the object increases, and the operator needs to check more images. It is therefore not preferable to increase the number of obtained previous images. That is, the number of obtained previous images should be limited to the necessary minimum, and this embodiment uses two previous images.

When the operator issues an instruction to start imaging upon checking images, the process advances from step S805a to step S1605. In steps S1605 to S1609, the insert determination unit 205 determines the insert condition of the breast in the breast insert portion 102 based on the difference between the number of direct irradiated pixels counted on the current projection image and that on the previous projection image. In this embodiment, the insert determination unit 205 determines the insert condition based on whether the difference in the number of direct irradiated pixels between the current image and the previous image falls within a predetermined range.

First of all, the first image is acquired in steps S1605 and S1606, and the number of pixels whose pixel values are equal to or more than a predetermined threshold $T_p$ is counted. The threshold $T_p$ is a value to be used for determination on whether a given pixel corresponds to a portion (to be referred to as a direct irradiated portion hereinafter), of an obtained image, on which the breast as an imaging target does not exist. That is, the pixel value of a given pixel is larger than $T_p$, it is determined that the pixel is a direct irradiated pixel; otherwise, it is determined that the breast is imaged. This number of direct irradiated pixels is saved in a variable $N_{Tp,i-1}$. Subsequently, the number of direct irradiated pixels on an image one frame preceding the current frame is saved in $N_{Tp,i-1}$.

In steps S1607 and S1608, the second image is acquired, and the number of direct irradiated pixels is counted by using the threshold $T_p$. This number of direct irradiated pixels is saved in a variable $N_{Tp,i}$. Subsequently, the number of direct irradiated pixels on an image of the current frame is saved in $N_{Tp,i}$.

Figure 18:
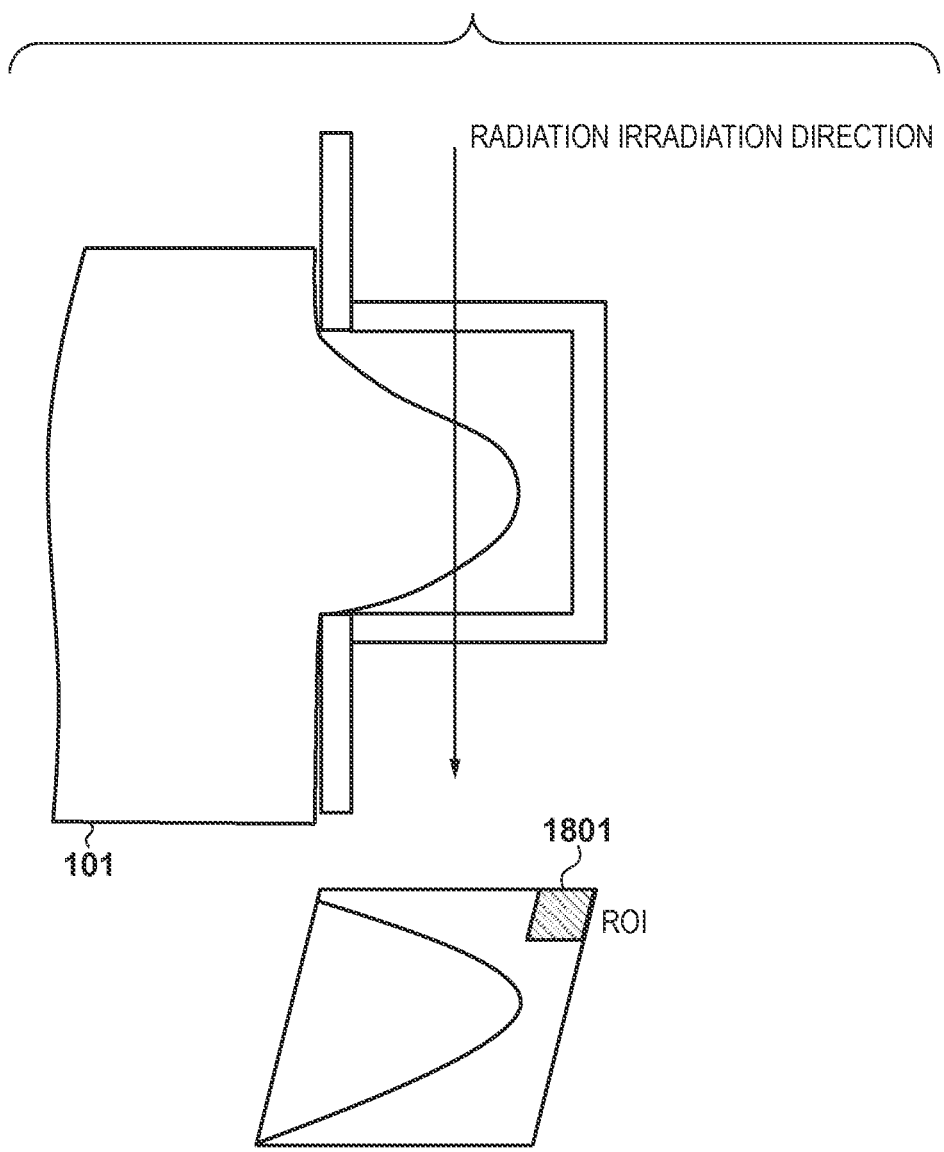
FIG. 18 is a view for explaining the position of a region of interest according to the fifth embodiment.

The following method is one form of a method of deciding the threshold $T_p$. For example, a portion of an imaging region is set as a region of interest (ROI). A representative value (an average value, median, or the like) and standard deviation of pixel values in the region of interest are obtained. A pixel value lower than the representative value by a predetermined value is set as the threshold $T_p$. In this case, the predetermined value is decided based on the standard deviation. In addition, it is possible to set, as a region of interest, a portion in which the breast is not depicted as much as possible, for example, a portion of a corner on a deep side when seen from the object, like a region 1801 in FIG. 18. There is also available, as a method of deciding the threshold $T_p$, a method of storing in advance direct irradiated portion values under a plurality of imaging conditions and calculating a direct irradiated portion value based on the stored values.

In step S1609, the difference between the number $N_{Tp,i-1}$ of direct irradiated pixels on the first image and the number $N_{Tp,i}$ of direct irradiated pixels on the second image is compared with thresholds $T_1$ and $T_2$. If the difference between the numbers of direct irradiated pixels exceeds the threshold $T_1$ or falls short of the threshold $T_2$, the incompletion of insertion is determined by regarding that the breast has come off the breast insert portion 102 or the breast has not been properly inserted. The imaging is then finished (forcibly terminated). In addition, if the difference between the number $N_{Tp,i-1}$ of direct irradiated pixels on the first image and the number $N_{Tp,i}$ of direct irradiated pixels on the second image is negative (the number of direct irradiated pixels has extremely decreased), the imaging is also finished (forcibly terminated). Obviously, in step S1609, a warning against the incompletion of insertion may be generated to allow the operator to select continuation of imaging, as in, for example, steps S807a and S807b in the first embodiment.

The following is the reason why it is possible to check the insert condition of the breast by comparing the difference in the number of direct irradiated pixels between current and previous obtained images with a threshold. In a state in which the breast is inserted into the breast insert portion 102 to a sufficient depth, the area of the breast on an obtained image becomes the largest. Therefore, the direct irradiated portion is minimized. On the other hand, when the breast comes off the breast insert portion 102, since nothing exists on the image, the image is dominated by a direct irradiated portion. If, therefore, a direct irradiated portion extremely increases in amount, it can be regarded that the breast has come off the breast insert portion.

If a direct irradiated portion decreases in amount, it can be regarded that although the breast was not inserted to a sufficient depth at the start of imaging, the breast has been inserted deeper when the body has moved than when imaging has started, resulting in a reduction in the direct irradiated portion. If, therefore, the direct irradiated portion has extremely decreased, it indicates that the breast has been inserted deeper than the initial depth, that is, the breast has not been inserted to the sufficient depth at the start of imaging.

Although the numbers of direct irradiated pixels on the immediately preceding image and the current image change because of the difference in imaging angle even in a state in which the breast is motionless, the changes are smaller than when the breast has come off. Therefore, the thresholds $T_1$ and $T_2$ are set to fall within the ranges in which the numbers of direct irradiated pixels change depending on the imaging angles. Note that the determination in step S1609 may be performed by using the absolute value of the above difference. In this case, for example, $|N_{Tp,i} - N_{Tp,i-1}| < T_1$ is determined, and only one threshold is required.

After the numbers of direct irradiated pixels are determined in step S1609, the number $N_{Tp,1}$ of direct irradiated pixels on the second image is saved in $N_{Tp,i-1}$ as the number of direct irradiated pixels on the image one frame preceding the next frame.

Subsequently, the process from step S1607 to step S808 is repeated from the third image to the end of imaging. During this repetition, the number of direct irradiated pixels on the nth image is obtained and saved in $N_{Tp,i}$ in step S1608. If the difference from $N_{Tp,i-1}$ in which the number of direct irradiated pixels on the (n−1)th image is saved becomes equal to or more than a threshold, the insert determination unit 205 forcibly terminates imaging; otherwise, the insert determination unit 205 saves in step S1610 the number of direct irradiated pixels on the nth image in $N_{Tp,i-1}$ to use it as the number of direct irradiated pixels on the image one frame preceding the next frame.

After the end of imaging, it is determined in step S809b whether the imaging is forcibly terminated. If NO in step S809b, a tomographic image is generated by reconstruction in step S813. In this case, the previous images obtained in steps S1602 and S1603 may be used for reconstruction. The generated tomographic image is displayed on the display device 109. The operator determines the necessity of re-imaging in step S1611. Note that although in this embodiment, tomography is not performed at the time of forcible termination, the imaging angle at the time of forcible termination may be stored to enable the generation of a tomographic image even at the time of forcible termination when it is possible to generate a tomographic image, as in step S812 in the first embodiment. In addition, although in the flowchart of FIGS. 16A and 16B, the processes in steps S810 and S812 in FIG. 8B are skipped, it is obvious that similar processes can also be executed in the fifth embodiment.

Depending on an imaging speed such as a frame rate or rotational speed, it is sometimes more preferable to perform comparison between the current image and a past image temporarily separated to some extent, for example, an image two frames preceding the current frame than comparison between the current image and the immediately preceding image. The insert determination unit 205 may therefore adjust images to be compared depending on an imaging speed.

In addition, in this embodiment, the insert condition of the breast is checked by using direct irradiated pixels. Likewise, however, the insert condition of the breast may be checked by comparing the number of pixels of the breast as an imaging target with a threshold. In addition, in the embodiment, the difference in the number of pixels is directly compared with a threshold. However, the difference in the number of pixels may be compared with a threshold after being normalized by the number of direct irradiated pixels on the previous frame $N_{Tp,i-1}$ like that indicated by expression (2):

$$\frac{(N_{Tp,i-1} - N_{Tp,i})}{N_{Tp,i-1}} \quad (2)$$

As described above, the fifth embodiment is configured to count the number of pixels whose pixel values exceed a predetermined pixel value with respect to the projection image obtained by repeating imaging for obtaining a tomographic image by rotating a radiation source 201 and a radiation detector 202 with respect to the breast insert portion 102. The insert condition of the breast in the breast insert portion 102 is then determined based on the difference between the number of pixels counted on the current projection image and that counted on the past projection image. Processing the images in this manner makes it possible to determine the insertion/non-insertion of the breast. An advantage of this embodiment is that it requires no detection device such as a contact detection unit. In addition, since radiography is performed before actual imaging, the operator can directly observe the interior of the breast insert portion 102. Furthermore, since the information of an immediately preceding image, which is required during imaging, is the number of direct irradiated pixels, it is possible to reduce the capacity of the storage device as compared with the method disclosed in patent literature 2, which requires all the information of the preceding image. In addition, unlike in patent literature 2, there is no need to perform subtraction for each pixel. This leads to high speed processing. On the other hand, unlike in the first to fourth embodiments, since previous images are obtained by radiation, the exposure dose may undesirably increase. However, it is possible to suppress an increase in exposure dose by reducing the frequency of imaging for obtaining an actual image by using previous images for the reconstruction of the actual image. Obviously, the fifth embodiment can be applied to both a sitting posture type breast tomography apparatus and a prone posture type breast tomography apparatus.

The first to fifth embodiments each have exemplified the method of checking the insert condition of the breast into the breast insert portion 102. Obviously, it is possible to more effectively check the insert condition of the breast by combining these methods. For example, when executing the fourth embodiment alone, it is necessary to stand by for the time threshold $T_0$ in advance to determine the insertion/non-insertion of the breast. However, combining this embodiment with the arrangement of the first embodiment makes it possible to determine a failure of insertion in advance because of a contact failure between a body portion of an object and the gantry front part 103. This can prevent unnecessary execution of suction. When an object is in a proper posture, it is possible to determine tight contact between a body portion of the object and the gantry front part 103 from the air pressure value sent from the air pressure detection unit 1301 as well as by contact determination on a body portion according to the first embodiment. It is therefore possible to perform more accurate determination than by executing the first and fourth embodiments alone.

In addition, when, for example, executing the first and fifth embodiments in combination, since it is possible to determine a failure of insertion in advance because of a contact failure between a body portion of an object and the gantry front part 103 before the acquisition of a radiographic image, it is possible to prevent unnecessary exposure to radiation for the acquisition of previous images. Furthermore, a checking operation using previous images can be performed in advance in addition to determination on contact with a body portion. Therefore, the insert condition of the breast can be determined more accurately than when the first and fifth embodiments are executed alone.

Although the above description has exemplified the breast tomography apparatus which performs tomography using X-ray transmission images, the present invention is not limited to this. For example, it is obvious that the present invention can be applied to a tomography apparatus using the photoacoustic effect based on X-rays or visible light, which is disclosed in Wenfeng Xia et. al. "An optimized ultrasound detector for photo acoustic breast tomography" Med. Phys. Vol. 40, 32901, 2013.

Each embodiment described above provides a breast tomography apparatus which can more accurately grasp the insert condition of the breast of an object and a method of controlling the apparatus.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-049313, filed Mar. 12, 2014, which is hereby incorporated by reference herein in its entirety.

What is claimed is:

1. A breast tomography apparatus comprising:
a gantry incorporating a radiation source and a radiation detector;
a breast insert portion, which is provided in the gantry and in which a breast of an object as an imaging target is to be inserted;
a detection unit, which is arranged on the gantry and includes a detection sensor configured to detect contact with the object;
a CPU; and
memory,
wherein the CPU and the memory are operatively coupled to function as a determination unit configured to determine an insert condition of the breast into the breast insert portion based on detection of contact by the detection sensor.

2. The breast tomography apparatus according to claim 1, wherein the detection sensor is arranged near a boundary between the gantry and the breast insert portion.

3. The breast tomography apparatus according to claim 1, wherein the detection sensor detects presence/absence of contact with the object at a plurality of positions on the gantry.

4. The breast tomography apparatus according to claim 3, wherein the detection sensor is configured to detect two-dimensional contact.

5. The breast tomography apparatus according to claim 3, wherein the determination unit further determines a posture of the object based on a distribution of information indicating the presence/absence of contact at the plurality of positions.

6. The breast tomography apparatus according to claim 3, wherein the determination unit further determines, based on a distribution of information indicating the presence/absence of contact at the plurality of positions, which one of left breast and right breast of the object is inserted into the breast insert portion.

7. The breast tomography apparatus according to claim 3, wherein the detection sensor detects pressures of contact with the object at the plurality of positions, and
the determination unit determines the insert condition of the breast into the breast insert portion based on a dispersion of pressures at the plurality of positions.

8. The breast tomography apparatus according to claim 3, wherein the detection sensor detects pressures of contact with the object at the plurality of positions, and
the determination unit determines the insert condition of the breast into the breast insert portion based on an average value of pressures detected from the plurality of positions.

9. The breast tomography apparatus according to claim 1, further comprising an insert informing unit configured to inform determination on the insert condition which is made by the determination unit.

10. The breast tomography apparatus according to claim 1, wherein the detection sensor detects a pressure of a contact of the object.

11. The breast tomography apparatus according to claim 1, wherein the detection sensor comprises a function for being energized when a pressure is applied.

12. The breast tomography apparatus according to claim 1, wherein the detection sensor comprises a function of a touch pad or a touch panel.

13. The breast tomography apparatus according to claim 1, wherein the detection sensor comprises a distance sensor, and if a distance detected by the distance sensor is smaller than a predetermined threshold, the detection sensor regards it as a contact of the object.

14. The breast tomography apparatus according to claim 1, wherein the determination unit determines, based on information indicating the presence/absence of contact with the object, a posture of the object.

15. The breast tomography apparatus according to claim 1, wherein the determination unit determines, based on information indicating the presence/absence of contact with the object, which one of left breast and right breast of the object is inserted into the breast insert portion.

16. A breast tomography apparatus comprising:
a gantry incorporating a radiation source and a radiation detector;
a breast insert portion, which is provided in the gantry and in which a breast as an imaging target is to be inserted;
a detection unit, including an illuminance detection sensor provided in the breast insert portion and configured to detect an illuminance;
a CPU; and
memory,
wherein the CPU and the memory are operatively coupled to function as a determination unit configured to determine an insert condition of the breast into the breast insert portion based on the illuminance detected by the illuminance detection sensor.

17. The breast tomography apparatus according to claim 16, wherein the determination unit determines the insert condition by comparing the illuminance detected by the illuminance detection sensor with a threshold.

18. The breast tomography apparatus according to claim 16, wherein the illuminance detection unit sensor is arranged on a bottom surface of the breast insert portion.

19. The breast tomography apparatus according to claim 16, wherein the illuminance detection unit sensor is arranged near a boundary between the breast insert portion and the gantry.

20. A method of controlling a breast tomography apparatus including: a gantry incorporating a radiation source and a radiation detector; and a breast insert portion, which is provided in the gantry, and in which a breast of an object as an imaging target is to be inserted, the method comprising:
a detection step of detecting contact with the object by using a detection sensor arranged on the gantry; and
a determination step of determining an insert condition of the breast of the object into the breast insert portion based on the contact detected in the detection step by the detection sensor.

21. A method of controlling a breast tomography apparatus including: a gantry incorporating a radiation source and a radiation detector; and a breast insert portion, which is provided in the gantry, and in which a breast as an imaging target is to be inserted, the method comprising:
a detection step of detecting an illuminance by using an illuminance detection sensor provided in the breast insert portion; and
a determination step of determining an insert condition of the breast into the breast insert portion based on the illuminance detected by the illuminance detection sensor.

22. A method of controlling a breast tomography apparatus including: a gantry incorporating a radiation source and a radiation detector; and a breast insert portion, which is provided in the gantry, and in which a breast as an imaging target is to be inserted, the method comprising:
a control step of repeatedly performing imaging for obtaining a projection image used to construct a tomographic image by rotating the radiation source and the radiation detector with respect to the breast insert portion;
a count step of counting a number of pixels whose pixel values exceed a predetermined pixel value based on a projection image obtained in the control step; and
a determination step of determining an insert condition of the breast in the breast insert portion based on a difference between the number of pixels counted in the count step on a current projection image and a past projection image.

* * * * *